(12) United States Patent
Lowenstein et al.

(10) Patent No.: US 7,910,111 B2
(45) Date of Patent: Mar. 22, 2011

(54) INHIBITORS OF N-ETHYLMALEIMIDE SENSITIVE FACTOR

(75) Inventors: Charles Lowenstein, Silver Spring, MD (US); Kenji Matsushita, Baltimore, MD (US); Craig Morrell, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1025 days.

(21) Appl. No.: 10/553,686

(22) PCT Filed: Apr. 15, 2004

(86) PCT No.: PCT/US2004/011655
§ 371 (c)(1),
(2), (4) Date: Nov. 3, 2006

(87) PCT Pub. No.: WO2004/091534
PCT Pub. Date: Oct. 28, 2004

(65) Prior Publication Data
US 2007/0173441 A1  Jul. 26, 2007

Related U.S. Application Data

(60) Provisional application No. 60/463,395, filed on Apr. 15, 2003.

(51) Int. Cl.
*A61K 39/12* (2006.01)

(52) U.S. Cl. .................................................... 424/204.1
(58) Field of Classification Search ........................ None
See application file for complete search history.

(56) References Cited

U.S. PATENT DOCUMENTS

| 5,981,192 A | 11/1999 | Bandman et al. |
| 2002/0037557 A1 | 3/2002 | Jing et al. |

OTHER PUBLICATIONS

Blanes-Mira et al, Society for Neuroscience Abstracts, 2001, vol. 27, No. 1, pp. 1017.*
Whiteheart et al. "N-Ethylmaleimide-sensitive Fusion Attachment proteins (SNAPS) Bind to aMulti-SNAP Receptor in Golgi Membranes" The Journal of Biological Chemistry, vol. 267. No. 17; Jun. 15, 1992, pp. 12239-12243.

* cited by examiner

*Primary Examiner* — Ali R. Salimi
(74) *Attorney, Agent, or Firm* — Whitham, Curtis, Christofferson & Cook, P.C.

(57) ABSTRACT

Methods and compositions for blocking exocytosis by inhibition of proteins that regulate exocytosis, such as N-ethylmaleimide Sensitive Factor (NSF), are provided. The compositions include multidomain fusion peptides containing a domain that causes the fusion peptide to cross the cellular membrane (e.g. a domain from the TAT protein of HIV) and a domain that inhibits NSF (e.g. a domain of NSF). Administration of the fusion peptide promotes anticoagulation, attenuates thrombosis, and decreases heart attack severity.

2 Claims, 11 Drawing Sheets

Figure 3
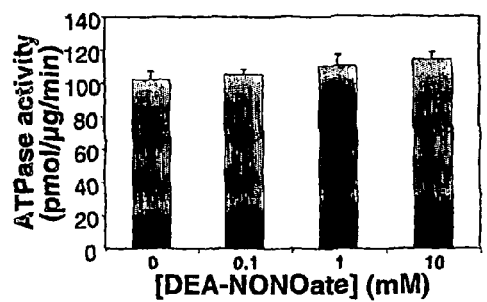
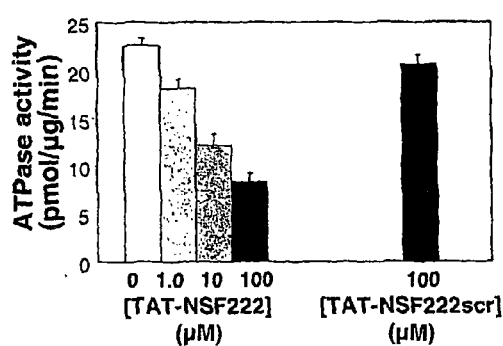
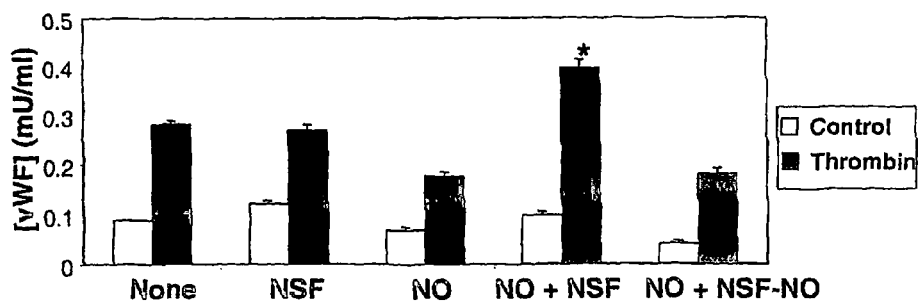

Figure 4
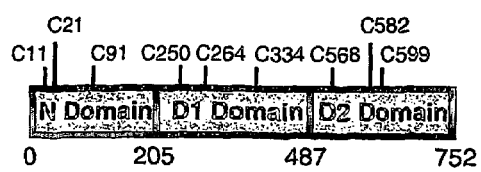
A
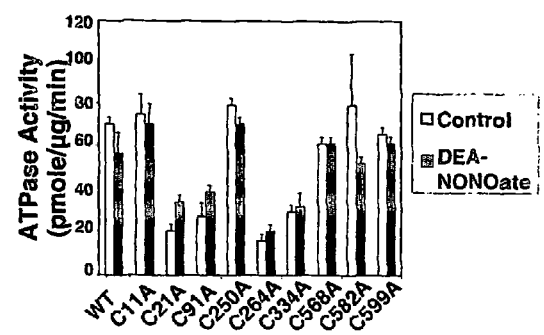
B
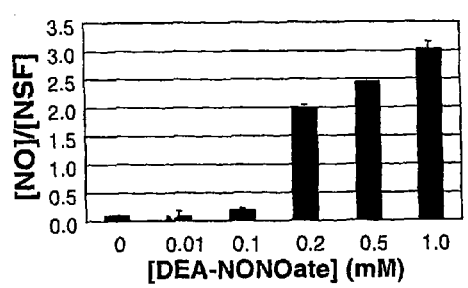
C
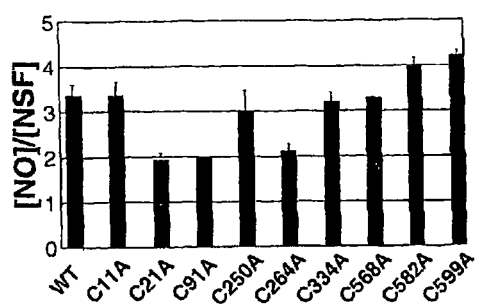
D

Figure 6
A
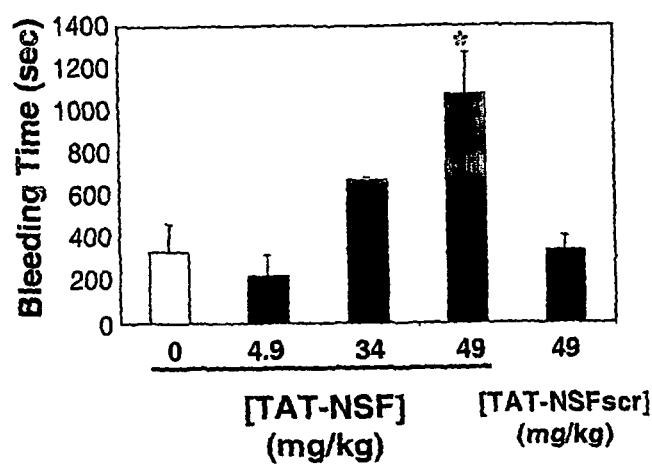
B
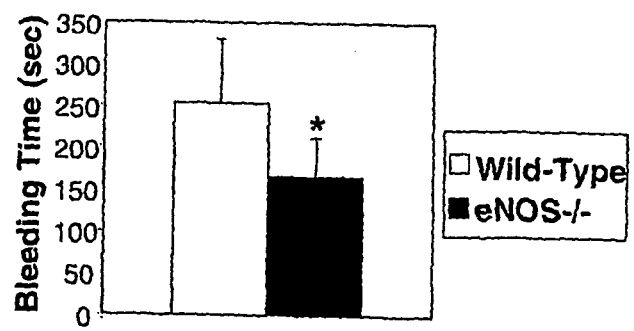

Figure 7
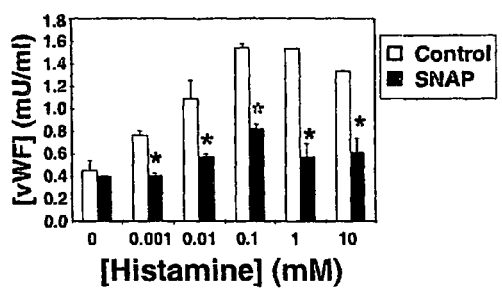
A
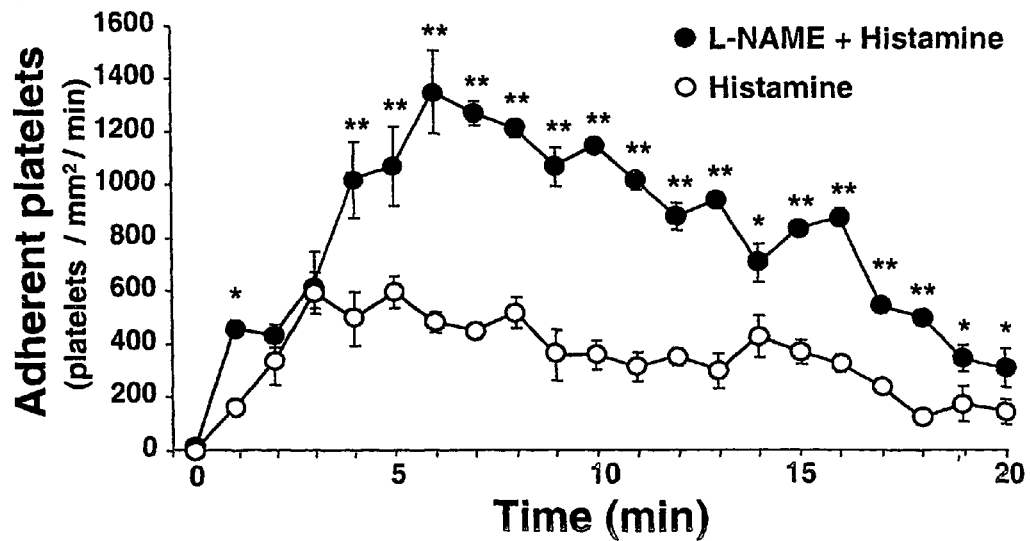
B

Figure 8
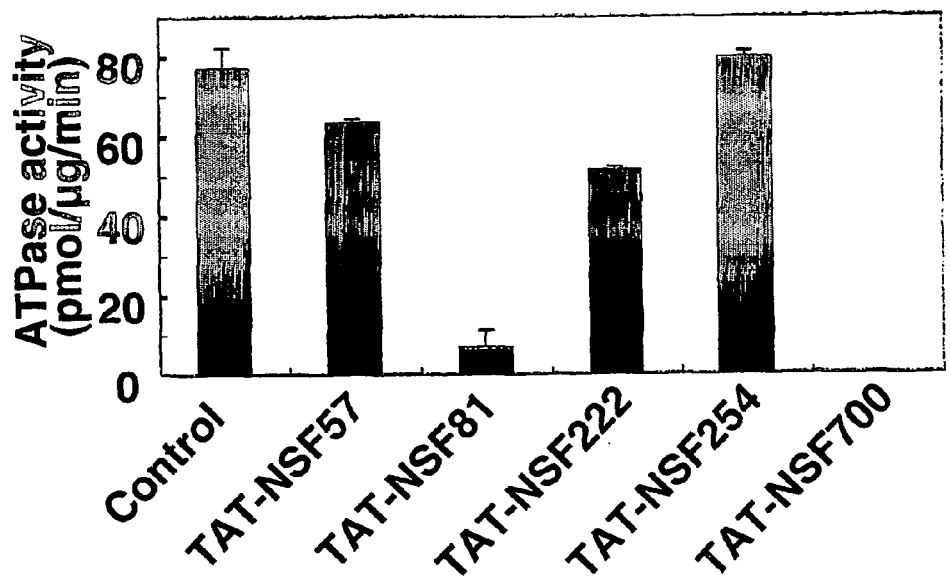
A
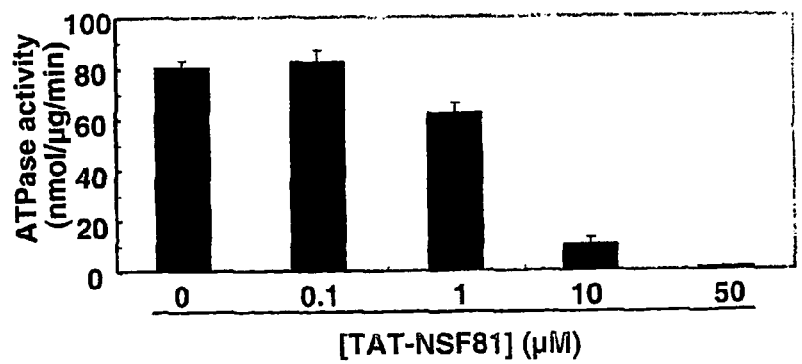
B

Figure 7
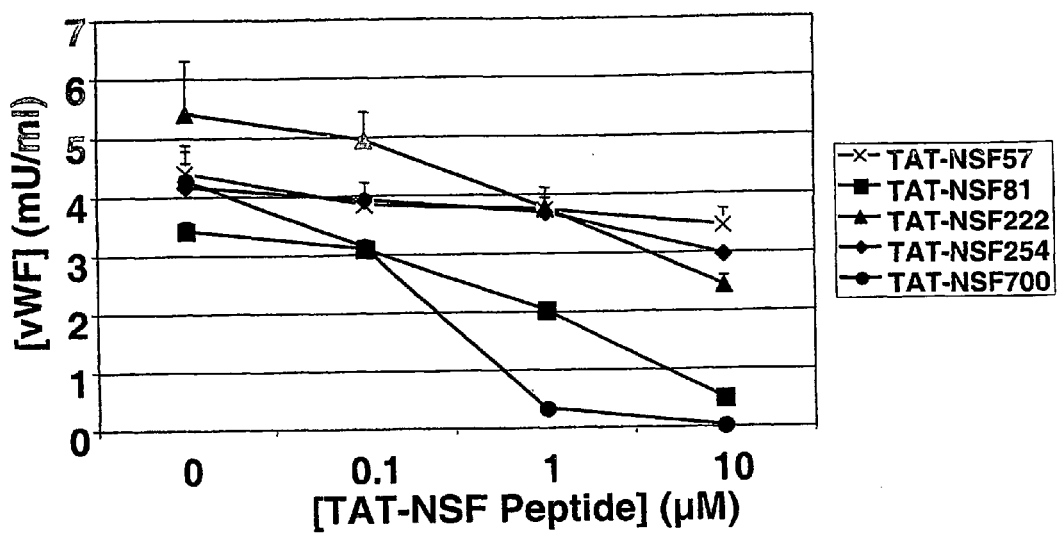
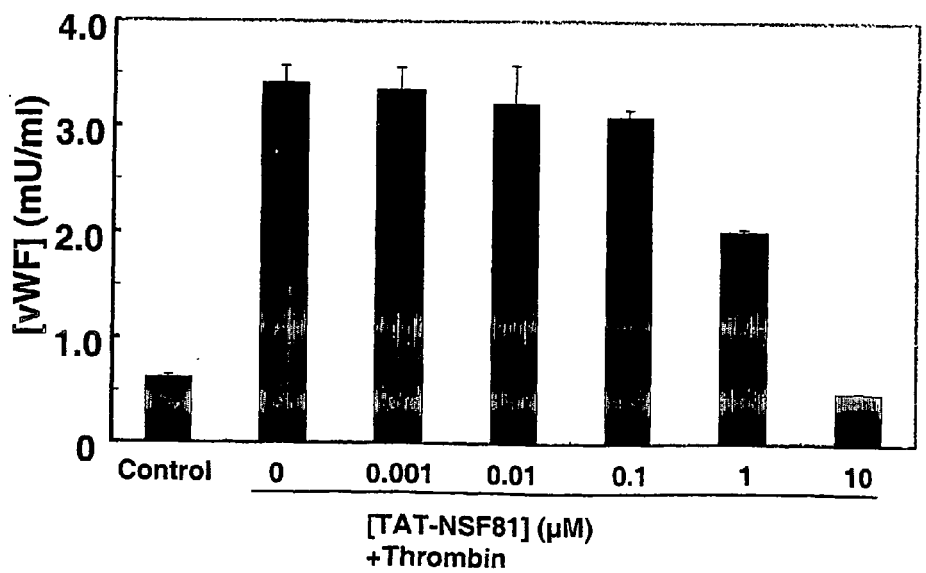

US 7,910,111 B2

INHIBITORS OF N-ETHYLMALEIMIDE SENSITIVE FACTOR

This application is a 371 PCT/US04/11655 filed Apr. 15, 2004 which claims benefit of 60/463,395 filed Apr. 15, 2003.

BACKGROUND OF THE INVENTION

1. Field of the Invention

The invention generally relates to inhibition of exocytosis by inhibiting the proteins that regulate exocytosis. In particular, the invention provides fusion peptides that cross cell membranes and inhibit N-ethylmaleimide Sensitive Factor (NSF), thus blocking exocytosis.

2. Background of the Invention

Exocytosis is a necessary and beneficial cellular process. However, disorders of exocytosis can result in severe and debilitating pathological conditions. These diseases include inflammatory and thrombotic disorders, including unstable angina, myocardial infarction, transient ischemic attack, and stroke. Thus, the ability to regulate exocytosis is a desideratum in the medical field.

One major pathway of exocytosis that is related to inflammation is exocytosis of Weibel-Palade bodies. Weibel-Palade bodies are endothelial granules, the contents of which include von Willebrand factor (vWF), P-selectin, tissue plasminogen activator, and CD63, and are known to mediate vascular inflammation and thrombosis. As such, Weibel-Palade exocytosis is an attractive target for regulation via medical intervention.

U.S. Pat. No. 6,461,616 to Shone et al. (Oct. 8, 2002) discloses recombinant polypeptides with two domains. The first domain allows the polypeptide to be translocated into a target cell or increases the solubility of the polypeptide, and the second domain allows inhibition of vesicle or plasma-membrane associated proteins essential to exocytosis, thereby inhibiting exocytosis.

U.S. Pat. No. 6,506,399 (Jan. 14, 2003) to Donovan discloses biodegradable botulinum toxin implants containing a therapeutic element which, when present in the cytoplasm of a neuron, inhibits exocytosis of acetylcholine from the neuron.

U.S. Pat. No. 6,623,980 B1 to Fisher et al., (Sep. 23, 2003) describes novel exocytotic polypeptides Exo1 and Exo2, and the use of the polypeptides to identify compositions which mediate exocytotic polypeptide bioactivity.

U.S. Pat. No. 6,632,440 to Quinn et al. (Oct. 14, 2003) describes methods and compounds useful for treating disorders related to the hypersecretion of mucus by inhibiting exocytosis in mucus secreting cells, and/or inhibiting neurotransmitter release from neuronal cells controlling or directing mucus secretion.

U.S. Pat. Nos. 5,817,789 (Oct. 6, 1998) and 6,027,921 (Feb. 22, 2000) to Heartlin et al., describe chimeric proteins which include a first domain that is a ligand-binding domain of a first receptor, and a carrier domain that binds a cell surface receptor other than the first receptor. The chimeric protein is transported into the cell upon binding of the carrier domain to the cell surface receptor.

Given the meager amount of methodology in the field, there is an ongoing need to develop novel compositions and methods for regulating exocytosis in order to treat pathological conditions that result from disorders of exocytosis. In particular, the prior art has thus far failed to provide adequate means of regulating exocytosis of Weibel-Palade bodies, and thus for treating or preventing related disorders.

SUMMARY OF THE INVENTION

The present invention provides novel fusion peptides that inhibit exocytosis, and methods for their use. The fusion peptides inhibit N-ethylmaleimide Sensitive Factor (NSF), thereby blocking exocytosis. In particular, the fusion peptides of the present invention are able to block exocytosis of Weibel-Palade bodies. The Examples of the present invention also demonstrate that administration of the fusion peptides to mammals results in 1) the promotion of anticoagulation (i.e. the fusion peptides act as anticoagulants); 2) treatment of thrombosis; and 3) a decrease in the severity of myocardial infarction (heart attack).

It is an object of this invention to provide a fusion peptide comprising a first sequence which promotes translocation of the fusion peptide across a membrane (preferably an endothelial cell membrane), and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8.

The invention further provides a method of inhibiting the activity of NSF. The method comprises the step of exposing the NSF to a fusion peptide comprising a first sequence which promotes translocation of the fusion peptide across a membrane and a second sequence that sensitive factor (NSF) activity. The activity that is inhibited may be the disassembly activity of NSF or the ATPase activity of NSF, or both. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8.

The invention also provides a method of inhibiting exocytosis in a cell. The method comprises the step of introducing into the cell, using a fusion peptide, a sequence that inhibits NSF activity. The fusion peptide comprises a first sequence which promotes translocation of the fusion peptide across a membrane and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8.

The invention further provides a method of providing anticoagulant activity to a patient in need thereof. The method comprises the step of administering a fusion peptide to the patient. The fusion peptide comprises a first sequence which promotes translocation of the fusion peptide across a membrane and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF.

In preferred embodiments, the fusion peptide is a peptide represented by SEQ ID NO: 2, SEQ ID NO: 5, SEQ ID NO: 6, SEQ ID NO: 7, or SEQ ID NO: 8. The fusion peptide is administered either prophylactically or therapeutically, or both.

The invention further provides a method of decreasing the size of myocardial infarction in a patient in need thereof. The method comprises the step of administering a fusion peptide to the patient. The fusion peptide comprises a first sequence which promotes translocation of the fusion peptide across a membrane and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8. The fusion peptide is administered either prophylactically or therapeutically, or both.

The invention also provides a method of treating thrombosis in a patient in need thereof. The method comprises the step of administering a fusion peptide to the patient. The fusion peptide comprises a first sequence which promotes translocation of the fusion peptide across a membrane and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8. The fusion peptide is administered either prophylactically or therapeutically, or both.

The invention further provides a method of inhibiting exocytosis of Weibel-Palade bodies from endothelial cells. The method comprises the step of inhibiting NSF activity in the endothelial cells by exposing the NSF to a fusion peptide. The fusion peptide comprises a first sequence which promotes translocation of the fusion peptide across a membrane and a second sequence that inhibits N-ethylmaleimide sensitive factor (NSF) activity. The fusion peptide may further comprise a third sequence that links the first sequence to the second sequence. The first sequence may comprise the peptide represented by SEQ ID NO: 1, and the second sequence may comprises an amino acid sequence from NSF. In preferred embodiments, the fusion peptide is a peptide represented by SEQ ID NO: 2, SEQ ID NO: 5, SEQ ID NO: 6, SEQ ID NO: 7, or SEQ ID NO: 8.

The invention further provides a method of transferring therapeutic compounds across cellular membranes in order to treat vascular and thrombotic disorders in a patient in need thereof. The method comprises the step of administering to the patient a fusion peptide, which comprises a first sequence which promotes translocation of the fusion peptide across a membrane, and a second sequence that inhibits a cellular process that activates vascular inflammation and thrombosis. In a preferred embodiment, the second sequence inhibits N-ethylmaleimide sensitive factor (NSF) activity. The fusion peptide may be the fusion peptide of claim 1. In another embodiment, the first sequence comprises the peptide represented by SEQ ID NO: 1. Further, the fusion peptide may also comprise a third sequence that links the first sequence to the second sequence. The second sequence of the fusion peptide may comprise an amino acid sequence from NSF. In preferred embodiments, the fusion peptide is a peptide selected from the group consisting of the peptides represented by SEQ ID NO: 2, SEQ ID NO: 5, SEQ ID NO: 6, SEQ ID NO: 7, and SEQ ID NO: 8. In a preferred embodiment, the cell is an endothelial cell.

BRIEF DESCRIPTION OF THE DRAWINGS

FIG. 3. NO inhibition of NSF. (A) NO does not inhibit NSF ATPase activity. A colorimetric assay was used to measure the ATPase activity of recombinant NSF that had been treated with DEA-NONOate. (n=3±S.D.) (B) TAT-NSF peptides inhibit NSF ATPase activity. A colorimetric assay was used to measure the ATPase activity of recombinant NSF that had been treated with TAT-NSF peptides. (C) Exogenous NSF restores vWF exocytosis in endothelial cells treated with NO. HAEC were pre-treated with 1 mM DEA-NONOate as above, permeabilized with SLO, incubated with recombinant NSF or nitrosylated recombinant NSF, stimulated with thrombin, and the amount of vWF in the media was measured (n=3±S.D.*P<0.01 for NO vs. NO+NSF).

FIG. 4. Cysteine residues mediating NSF activity. (A) Schematic of NSF. (3) Cysteine residues mediating ATPase activity of NSF. Wild-type NSF and mutant NSF were expressed and purified, treated with 1 mM DEA-NONOate or DEA, and the ATPase activity was measured as above. Mutagenesis of Cys at 21, 91, 264, and 334 partially inhibits NSF ATPase activity. NO does not inhibit ATPase activity of wild-type or mutant NSF (n=3±S.D.). (C) Nitrosylation of NSF in vitro. DEA-NONOate was added to recombinant wild-type NSF, and the molar ratio of nitrosothiols per NSF molecule was measured by the Saville reaction. Each molecule of NSF can contain a maximum of 3 nitrosothiols (n=3±S.D.). (D) Identification of nitrosylated cysteine residues in NSF. DEA-NONOate was added to recombinant NSF mutants, and the molar ratio of nitrosothiols per NSF molecule was measured by the Saville reaction. Mutation of C21 or C91 or C264 decreases the nitrosothiol content of nitrosylated NSF (n=3-5±S.D.).

FIG. 6. NSF is nitrosylated and inhibits exocytosis in vivo. (A) Inhibition of NSF in mice prolongs bleeding time. Anesthetized mice were injected with PBS or the TAT-NSF222 peptide that inhibits NSF, and after 45 min the distal tip of the tail was amputated and the bleeding time was measured. Bleeding that continued longer than 20 min was recorded as 20 min (n=3-6±S.D.*P<0.01 for TAT-NSF vs. TAT-NSFscr at 49 mg/kg). (B) Endogenous NO prolongs bleeding time in mice. The distal tip of the tail was amputated from wild-type and eNOS null mice, and the bleeding time was measured (n=7-8±S.D.*P=0.01 for wild-type vs. eNOS null).

FIG. 7. NO inhibits exocytosis in vivo and consequently platelet adhesion to endothelium. (A) Exogenous NO inhibits histamine induced exocytosis in vitro. HAEC were pre-treated with the NO donor SNAP 100 µM for 4 h, and then stimulated with histamine for 1 h, and the amount of released vWF was measured as above (n=2±S.D.*P<0.05 vs. 0 µM) (B) Inhibition of endogenous NOS increases platelet adherence to venules in mice over time. Mice were pre-treated (filled circle) or not (white circle) with L-NAME and then transfused with calcein-AM labeled platelets as above. Intravital microscopy was used to visualize fluorescent platelets transiently adhering to mesenteric venules 0-20 min after superfusion with 10 µl of 1 mM histamine. Quantitative analysis of platelet adhesion as a function of time after the secretagogue application is shown (n=4-5 mice±S.E.M.*P<0.05 and **P<0.01 vs. non-treated).

FIG. 8. (A) Effect of TAT-NSF peptides on NSF ATPase activity. A colorimetric assay was used to measure the ATPase activity of recombinant NSF that had been treated with 10 µM TAT-NSF peptides (n=3±S.D.). (B) TAT-NSF81 inhibits NSF ATPase activity. A colorimetric assay was used to measure the ATPase activity of recombinant NSF that had been treated with TAT-NSF 81 (n=3±S.D.).

FIG. 9. (A) Effect of TAT-NSF peptides on thrombin-induced vWF exocytosis from HAEC. HAEC were pre-treated with TAT-NSF peptides for 20 min, and then treated with thrombin, and the amount of vWF released into the media was measured by an ELISA. (n=3±S.D.) (B) Effect of TAT-NSF peptides on thrombin-induced vWF exocytosis from HAEC. HAEC were pre-treated with TAT-NSF81 for 20 min, and then treated with thrombin, and the amount of vWF released into the media was measured by an ELISA. (n=3±S.D.)

DETAILED DESCRIPTION OF THE PREFERRED EMBODIMENTS OF THE INVENTION

Figure 1:
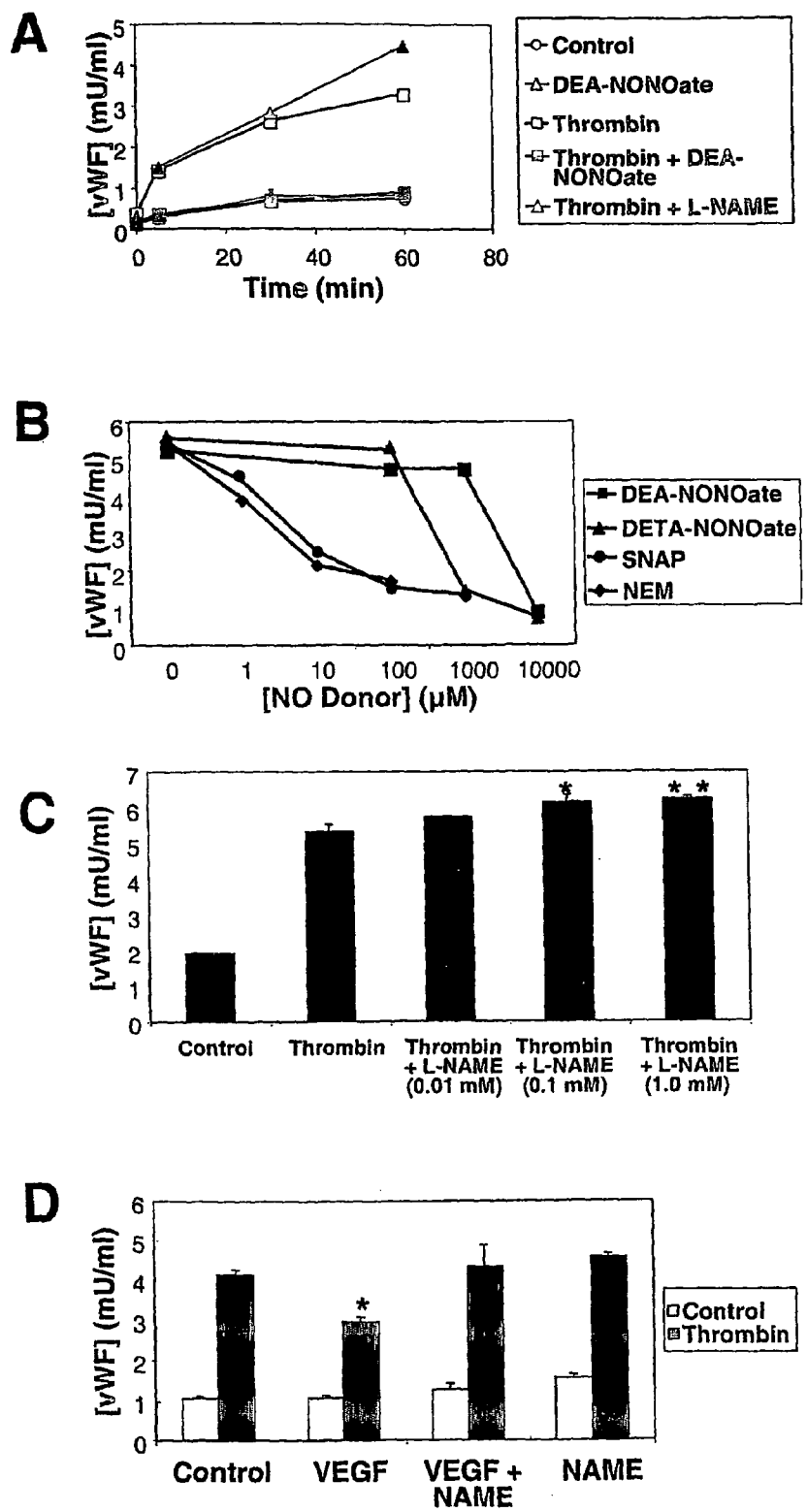
FIG. 1. NO inhibits vWF release from human aortic endothelial cells. (A) Time course. HAEC were pre-treated with DEA as a control or the NO donor DEA-NONOate or the NOS inhibitor L-NAME, and then incubated with thrombin for 1 h. The amount of vWF released from cells into the media was measured by an ELISA (n=3-5±S.D.). Exogenous NO inhibits exocytosis, and L-NAME inhibition of endogenous NOS increases exocytosis. (B) Dose response. HAEC were pre-treated with DEA-NONOate for 10 min, DETA-NONOate for 16 h, SNAP for 6 h, or NEM for 1 h), and then incubated with thrombin for 1 h. The amount of vWF released from cells was measured by an ELISA (n=3-5±S.D.). (C) Inhibition of endogenous NOS increases vWF release. HAEC were pre-treated with L-NAME for 16 h, incubated with thrombin for 1 h, and vWF released from cells was measured as above (n=2±S.D.*P<0.06 vs. Thrombin. **P=0.03 vs. Thrombin). (D) Activation of endogenous NOS decreases vWF release. HAEC were pre-treated with media or 1 mM L-NAME for 16 h, stimulated with 50 ng/ml VEGF for 2 h, and then incubated with thrombin. The amount of released vWF was measured as above (n=3±S.D.*P<0.01 vs. Control).

The present invention provides fusion peptides that inhibit exocytosis and methods for their use. The peptides inhibit exocytosis by inhibiting the activity of proteins that regulate exocytosis, such as N-ethylmaleimide sensitive factor (NSF). In a preferred embodiment of the invention, the fusion peptides are used to inhibit exocytosis of Weibel-Palade bodies.

The fusion peptides of the present invention, which may also be referred to as chimeric peptides, contain at least two distinct regions or domains. The first domain is a sequence of amino acids that promotes translocation of the fusion peptide across the cellular membrane, preferably the membrane of endothelial cells. In general, this translocation domain will be in the range of about 10 to about 30 amino acids in length, and preferably about 11 amino acids in length. In a preferred embodiment of the invention, the first domain is an 11 amino acid residue polypeptide fragment derived from the human immunodeficiency virus TAT domain (YGRKKRRQRRR, SEQ ID NO:1). However, those of skill in the art will recognize that other peptide sequences also exist which can perform the function of mediating translocation of the fusion peptide across the cellular membrane. Examples of such sequences include but are not limited to the Antennapedia protein from *Drosophila* and the VP22 protein from herpes simplex virus.

The second domain of the fusion peptides of the present invention is a domain that inhibits the activity of a protein that regulates exocytosis, such as NSF. By "inhibits the activity of NSF" we mean that either the NSF disassembly activity or the ATPase activity, or both, is inhibited. The level of inhibition of the activity of NSF will typically be in the range of from about 25% to about 100% inhibition, or preferably from about 50% about 100% inhibition, and most preferably from about 75% to about 100% inhibition, as measured by assays that are well-known to those of skill in the art and described herein in the Examples section. In general, this NSF-inhibiting domain will be in the range of about 10 to about 50 amino acids in length, and preferably about 20 to about 25 amino acids in length. In preferred embodiments of the invention, the NSF-inhibiting domain of the fusion peptides of the present invention is a sequence of amino acids from the NSF protein itself that has been shown to inhibit NSF activity. For example, in Example 2 below, five fusion peptides containing five different amino acid sequences from NSF were tested and shown to inhibit exocytosis, when used according to the methods of the present invention. Those of skill in the art will recognize that the NSF-inhibitory domain of the fusion peptides of the present invention need not be limited to the exact amino acid sequences presented in the Examples. Other amino acid sequences from NSF are also known to inhibit NSF and may also be used in the practice of the present invention. Examples of such sequences include but are not limited to QSVISPDWDFTKMGIGGLDK (SEQ ID NO: 9), GLDKEFNSIFRRAFASRVFPPE (SEQ ID NO: 10), TGKTLIARKIGTMLNAREPK (SEQ ID NO: 11), and KYVGESEANVRRLFAEAEE (SEQ ID NO: 12).

In addition, the amino acid sequence of the second, NSF-inhibitory domain of the fusion peptides of the present invention need not be from the NSF protein. Those of skill in the art will recognize that other amino acid sequences from other sources exist which also inhibit NSF, and which may be used in the practice of the present invention. Examples of such proteins which are targets of NSF include but are not limited to: soluble NSF attachment protein (SNAP isoforms), soluble NSF attachment protein receptor proteins (SNARE isoforms). Sequences derived from these NSF targets include but are not limited to amino acid residues of alpha-SNAP that interact with NSF, amino acid residues of syntaxin-4 that interact with NSF, amino acid residues of syntaxin-4 that interact with alpha-SNAP, and amino acid residues of syntaxin-4 that interact with other SNARE proteins.

The fusion peptides of the present invention may also include a third domain which is a "linker" or "spacer" domain. The linker domain does not necessarily possess either the ability to mediate translocation or inhibition of NSF. Rather, the linker domain serves to link the two primary domains together while introducing a space between the two primary domains, allowing the primary domains greater three-dimensional, steric freedom, or simply facilitating in the fusion peptide design. In general, the linker domain will be in the range of about 1 to about 10 amino acids in length, and preferably about 3 to about 5 amino acids in length. An exemplary linker domain, GGG, is described in the Examples section below. However, those of skill in the art will recognize that many other suitable sequences may also be employed, so long as the linking sequence is of a convenient length, and contains amino acids that do not interfere with the functions of the two primary domains.

Exemplary primary sequences of fusion proteins for use in the practice of the present invention are given in the Examples section below. However, those of skill it the art will recognize that variants of those sequences may also be successfully employed. Many changes in the primary sequence such as insertions, deletions, substitutions, etc., may be tolerated by the exemplary fusion peptides without compromising their effectiveness. A variant peptide can differ in amino acid sequence by one or more substitutions, deletions, insertions, inversions, fusions, and truncations or a combination of any of these. Substitutions may be both conservative and non-conservative, although conservative substitutions are preferable, since conservative substitutions are likely to be phenotypically silent. Such substitutions are those that substitute a given amino acid in a polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247: 1306-1310 (1990).

Variant peptides would be peptides having at least about 70% to about 100% homology with those sequences, and preferably about 80% to about 100% homology, and more preferably about 90% to about 100% homology, and most preferably about 95% to 100% homology. By a polypeptide having an amino acid sequence at least, for example, 90% homologous to a reference amino acid sequence of the present invention, it is intended that the amino acid sequence of the variant polypeptide is identical to the exemplary sequence except that the variant polypeptide sequence may include up to one amino acid alteration per each 10 amino acids of the exemplary amino acid sequence. In other words, to obtain a polypeptide having an amino acid sequence at least 90% identical to an exemplary amino acid sequence of the present invention, up to 10% of the amino acid residues in the exemplary sequence may be inserted, deleted, substituted, etc., with another amino acid. These alterations of the exemplary sequence may occur at the amino or carboxy terminal positions of the exemplary amino acid sequence or anywhere between those terminal positions, interspersed either individually among residues in the exemplary sequence or in one or more contiguous groups within the exemplary sequence. Such variant peptides are considered to be substantially homologous to the exemplary fusion peptides of the present invention.

The fusion peptides of the present invention may be made by chemical synthesis according to methods that are well known to those of skill in the art. Alternatively, they may be synthesized by recombinant technology by transcription and translation of suitable nucleic acid (e.g. DNA, RNA) templates encoding the peptides. Such recombinant technology, including suitable vectors and translation systems, are well-known to those of skill in the art. The encoding DNA may be identical in sequence to a DNA that encodes the amino acid sequence of interest in nature i.e. that corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein or portion or a protein). An example would be the DNA that encodes the 11 amino acid peptide from the TAT domain of HIV. Alternatively, due to the redundancy of the genetic code, many DNA sequences may be devised that, when transcribed and translated, would result in the production of the exemplary fusion peptides of the present invention. Any such DNA sequence may be utilized to produce the fusion peptides of the present invention. Further, suitable fusion peptides for use in the present invention may be defined as any fusion peptide that is produced from a DNA molecule which contains nucleotide sequences encoding the domains of the fusion peptides, those nucleotide sequences being identical to the sequences encoding the domains in the original source of the domain (e.g. the TAT domain of HIV, and the human NSF gene), or exhibiting at least about 70% to about 100% homology with those sequences, and preferably about 80% to about 100% homology, and more preferably about 90% to about 100% homology, and most preferably about 95% to 100% homology. By a subject nucleotide sequence being at least, for example, 90% homologous to a reference nucleotide sequence, it is intended that the subject nucleotide sequence is identical to the reference sequence except that the subject nucleotide sequence may include up to one nucleotide alteration per each 10 nucleotides of the nucleotide sequence. In other words, in a subject nucleotide sequence that is at least 90% identical to reference sequence, up to 10% of the nucleotides in the reference sequence may be inserted, deleted or substituted with another nucleotide. Such variant nucleotide sequences are considered to be substantially homologous to nucleotide sequences encoding the domains of the exemplary fusion peptides of the present invention, as isolated from the organism of origin of the domain.

In addition, the domains of the fusion peptides of the present invention may be encoded by nucleic acid molecules that hybridize under stringent conditions to the nucleic acids encoding the domains in the organism from which the domain was originally isolated. For example, a fusion peptide of the present invention may be defined as: a peptide with a translocation domain encoded by a nucleic acid sequence of HIV that encodes the 11 amino acid residues of SEQ ID NO:1, or a translocation domain that is encoded by a nucleic acid sequence that hybridizes to SEQ ID NO:1 under stringent conditions; and a peptide with an NSF-inhibitory domain that is encoded by a nucleic acid sequence of NSF (e.g. human NSF), or an NSF-inhibitory domain encoded by a nucleic acid sequence that hybridizes under stringent conditions to a nucleic acid sequence of NSF.

The invention also encompasses fusion peptides having a lower degree of identity but having sufficient similarity so as to perform one or more of the same functions performed by the fusion peptides described herein. Fully functional variants typically contain only conservative variation or variation in non-critical residues or in non-critical regions. Functional variants can also contain substitution of similar amino acids, which result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region. Variants can be naturally-occurring or can be made by recombinant means or chemical synthesis to provide useful and novel characteristics for the polypeptide. Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity. Sites that are critical can also be determined by structural analysis such as crystallization, nuclear magnetic resonance or photoaffinity labeling (Smith et al., J. Mol. Biol. 224:899-904 (1992); de Vos et al. Science 255: 306-312 (1992)).

As used herein, the term "hybridizes under stringent conditions" is intended to describe conditions for hybridization and washing under which nucleotide sequences encoding fusion peptides at least 55% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. One example of stringent hybridization conditions are hybridization in 6× sodium chloride/sodium citrate (SSC) at about 45 degrees C., followed by one or more washes in 0.2×SSC, 0.1% SDS at 50-65 degrees C.

The present invention also provides methods for using the fusion peptides of the present invention in order to inhibit NSF in a patient, to inhibit exocytosis in a patient, to promote anticoagulation in a patient, and to decrease the size of myocardial infarction in a patient. Each of these methods includes a step of administering to the patient an amount of a fusion peptide of the present invention sufficient to bring about the desired outcome, i.e. inhibition of NSF, inhibition of exocytosis, promotion of anticoagulation, and decreasing the size of myocardial infarction. The fusion peptides of the present invention may be administered either prophylactically to prevent symptoms of an exocytosis related disorder, or therapeutically to treat the disorder, or both. The amount of fusion peptide that is administered will vary from patient to patient, depending on many factors such as gender, age, general health, extent of disease progression, etc. and is best determined by a skilled practitioner such as a physician. However, in general the amount of fusion peptide that is administered will be in the range of about 1 to about 100 mg/kg, and preferably in the range of about 10 to about 50 mg/kg. Further, more than one type of fusion peptide may be administered.

Administration of the pharmaceutical preparation containing the fusion peptide of the present invention may be accomplished by any of a variety of methods that are well known to those of skill in the art, including but not limited to oral or parenteral, including intravenously, intramuscularly, subcutaneously, etc., or by other routes (e.g. transdermal, sublingual, aerosol, etc.). Administration is preferably by intravenous routes. The administration of pharmaceutical compositions of the present invention can be intermittent, or at a gradual or continuous, constant or controlled rate to a patient. In addition, the time of day and the number of times per day that the pharmaceutical formulation is administered can vary.

The fusion peptides can be administered in a substantially purified form or in a pharmaceutically acceptable formulation including suitable elixirs, binders, and the like or as pharmaceutically acceptable salts or other derivatives. The preparation typically includes at least one fusion peptide of the present invention in an amount ranging from about 1% to about 100% of the weight of the preparation. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1-99% of the composition and the vehicular "carrier" will constitute 1-99% of the composition. The pharmaceutical compositions of the present invention may include any suitable pharmaceutically acceptable additives or adjuncts to the extent that they do not hinder or interfere with the therapeutic effect desired of the fusion peptide.

The fusion peptides of the present invention may be used to treat or prevent a wide variety of disorders related to exocytosis, including but not limited to thrombotic disorders (e.g. myocardial infarction, stroke, deep venous thrombosis, pulmonary embolus, hemolytic uremic syndrome, thrombotic thrombocytopenic purpura), sepsis, microangiopathic hemolytic anemia, autoimmune diseases, and the like. Any disorder that can be ameliorated by the administration of the fusion peptides of the present invention may be treated by administration of the fusion peptides of the present invention.

In order to treat such conditions, the present invention also provides a method of transferring therapeutic compounds across cellular membranes in order to treat vascular and thrombotic diseases. In the practice of the method, a fusion peptide with a first domain containing a translocation domain, one example of which is a sequence derived from TAT (e.g. the 11 amino acid sequence represented by SEQ ID NO:1) and a second domain comprising the therapeutic compound. In some embodiments, the therapeutic compound is a peptide, for example, a peptide that inhibits a cellular process that activates vascular inflammation and thrombosis. In one embodiment of the invention, NSF activity is inhibited.

The foregoing examples are provided in order to illustrate the practice of the present invention but should in no way be considered limiting. Example 1 demonstrates that NSF regulates exocytosis of Weibel-Palade bodies, and that inhibitors of NSF (both NO and novel fusion peptides of the invention) inhibit exocytosis of Weibel-Palade bodies. Example 2 demonstrates that several variants of the fusion peptides of the present invention inhibit NSF, inhibit endothelial cell exocytosis, and prolong bleeding time in mammals. Example 3 demonstrates that administration of the fusion peptides of the present invention decreases the size of myocardial infarctions in mammals.

EXAMPLES

Example 1

Nitric Oxide Regulation of Exocytosis by S-Nitrosylation of N-ethylmaleimide Sensitive Factor Nitric oxide (NO) is a messenger molecule produced by the NO synthase (NOS) isoforms neuronal NOS (nNOS, or NOS1), inducible NOS (iNOS, or NOS2, and endothelial NOS (eNOS, or NOS3) (Nathan and Xie, 1994; Stamler et al., 1992). All three NOS isoforms can be found in the vasculature—NOS1 in nerve fibers in the adventitia, NOS2 in vascular smooth muscle cells and in infiltrating macrophages during vascular inflammation, and NOS3 in endothelial cells—and NO has a variety of effects upon vascular cells (Christopherson and Bredt, 1997; Michel and Feron, 1997; Papapetropoulos et al., 1999; Radomski and Moncada, 1993). NO relaxes smooth muscle, inhibits smooth muscle cell migration and proliferation, and decreases platelet adherence and aggregation. NO also inhibits vascular inflammation: atherosclerosis is increased in mice deficient in NOS2 or NOS3, transplant vasculopathy is exacerbated in mice deficient in NOS2 or NOS3, transplant vasculopathy is exacerbated in mice lacking NOS2, and the response to vascular injury is accelerated in mice lacking NOS3 null mice (Kuhlencordt et al., 2001a; Rudic et al., 1998). However, the molecular basis for the anti-inflammatory properties of NO is not completely understood.

NO may regulate vascular inflammation in part by inhibiting exocytosis of Weibel-Palade bodies (Qian et al., 2001). Discovered by Weibel and Palade in 1964, Weibel-Palade bodies are cigar shaped endothelial organelles, the contents of which mediate vascular thrombosis and inflammation (Wagner, 1993). In resting endothelial cells, Weibel-Palade bodies remain in the cytoplasm. However, a variety of agonists such as thrombin, complement, and leukotrienes, can induce their rapid release from endothelial cells (Birch et al., 1994; Datta et al., 1995; Foreman et al., 1994; Vischer et al., 1995; Vischer and Wollheim, 1997). Weibel-Palade bodies contain von Willebrand factor (vWF), P-selectin, tissue plasminogen activator, and CD63 (Bonfanti et al., 1989; Huber et al., 2002; McEver et al., 1989; Vischer and Wagner, 1993; Wagner et al., 1982; Weibel and Palade, 1964). Weibel-Palade bodies also contain interleukin-8 following inflammatory stimulation of endothelial cells (Utgaard et al., 1998; Wolff et al., 1998). Exocytosis of Weibel-Palade bodies leads to the release of vWF, which promotes platelet adhesion and aggregation, as well as prolonging the half-life of factor VIII (Ruggeri, 1997). Weibel-Palade body exocytosis also leads to the translocation of the transmembrane protein P-selectin to the endothelial cell plasma membrane, where it regulates leukocyte rolling and extravasation (Larsen et al., 1989; McEver et al., 1989; Springer, 1994). IL-8, a chemokine released by Weibel-Palade body exocytosis, can activate neutrophils, further promoting leukocyte extravasation.

Secretagogues such as thrombin, histamine, fibrin, complement, leukotrienes, and ATP, trigger Weibel-Palade body exocytosis within minutes. Although the molecular machinery regulating Weibel-Palade body exocytosis is not defined, it is likely that proteins that regulate vesicle trafficking in other cells also regulate Weibel-Palade body exocytosis in endothelial cells.

Vesicle trafficking involves targeting of a vesicle to a specific membrane, priming of the vesicle, and membrane fusion, followed by recycling of trafficking components (Jahn et al., 2003; Jahn and Sudhof, 1999; Mellman and Warren, 2000; Rothman and Wieland, 1996; Springer et al., 1999; Wickner and Haas, 2000). At least four classes of proteins regulate membrane fusion: Rab and Rab effectors which regulate vesicle tethering to target membranes; soluble NSF receptor (SNARE) proteins which are localized to vesicle and target membranes and assemble into stable ternary complexes; members of the Sec1/Munc18 protein family, and N-ethylmaleimide sensitive factor (NSF), along with the family of soluble NSF attachment proteins (SNAP), which plays a critical role in regulating vesicle trafficking by hydrolyzing ATP and disassembling SNARE complexes.

NSF was first identified as a cytosolic protein necessary for in vitro reconstitution of intercisternal Golgi transport, and subsequently was shown to regulate intracellular transport in yeast, nematodes, insects, and mammals (Block et al., 1988; Kaiser and Schekman, 1990; Malhotra et al., 1988; May et al., 2001). NSF forms homohexamers, hydrolyzes ATP, and alters the conformation of the stable SNARE complex (Block et al., 1988; Malhotra et al., 1988). NSF is composed of three domains, an N-terminal domain, and two homologous ATP binding domains. The N-terminal domain (residues 1-205) interacts with members of the SNAP family, which in turn interact with SNARE molecules. The D1 domain (residues 206-488) hydrolyzes ATP, and provides the mechanical force to disassemble SNARE complexes. The D2 domain (residues 489-744) mediates NSF hexamerization.

Although NSF regulates vesicle trafficking and exocytosis, the regulation of NSF is not well understood. Sensitivity to NEM suggests that NSF might be regulated by S-nitrosylation, a mechanism by which NO modulates protein functions (Stamler, 1994; Stamler et al., 2001; Stamler et al., 1992).

Exogenous and Endogenous NO Inhibits Weibel-Palade Body Exocytosis

To explore the effect of NO upon granule exocytosis, thrombin induced exocytosis of Weibel-Palade bodies from human aortic endothelial cells (HAEC) which release von Willebrand's Factor (vWF) was studied. HAEC was pre-treated with an NO donor 2-(N,N-diethylamino)-diazenolate-2-oxide (DEA-NONOate) 10 mM or with DEA as a control, stimulated the cells with thrombin 1 U/ml for 1 h, and the amount of vWF released into the media was then measured. Thrombin induces a rapid release of vWF from HAEC (FIG. 1A). However, exogenous NO blocks the effects of thrombin (FIG. 1A). Endogenous NO produced from endothelial cells also inhibits vWF release, since 1 mM L-nitroarginine-methyl-ester (L-NAME) inhibition of NOS for 16 h increases the amount of vWF released after thrombin stimulation (FIG. 1A). NO inhibition of vWF release is dose-dependent. HAEC was then pre-treated with increasing amounts of various NO donors, including a rapidly releasing NO donor DEA-NONOate for 10 min, a slowly releasing NO donor DETA-NONOate for 16 h, or a nitrosothiol S-nitroso-penicillamine (SNAP) for 6 h; alternatively, cells were treated with NEM for 1 h. Pre-treatment with any one of these reagents inhibits thrombin induced vWF release (FIG. 1B).

The role of endogenous NO in the regulation of Weibel-Palade body exocytosis was then explored. HAEC was pre-treated with L-NAME for 16 h in order to inhibit endogenous NOS, and then the cells were stimulated with 1 U/ml thrombin for 1 h and vWF release was measured. L-NAME increases thrombin stimulated vWF release in a dose-dependent manner (FIG. 1C). (The iNOS inhibitor 1400W had no effect (data not shown)). HAEC was next pre-treated with vascular endothelial growth factor (VEGF) in order to activate endogenous NOS3. Cells were incubated with 50 ng/ml VEGF or control for 2 h, and then stimulated with thrombin. VEGF treatment decreases thrombin stimulated vWF release (FIG. 1D). L-NAME 1 mM blocks the effects of VEGF treatment, implying that NO mediates VEGF inhibition of exocytosis (FIG. 1D).

Since L-NAME inhibition of NOS increases exocytosis, and since VEGF activation of NOS decreases exocytosis, taken together these data suggest that endogenous NO regulates endothelial cell exocytosis.

SNARE Molecules Regulate Weibel-Palade Body Exocytosis

Figure 2:
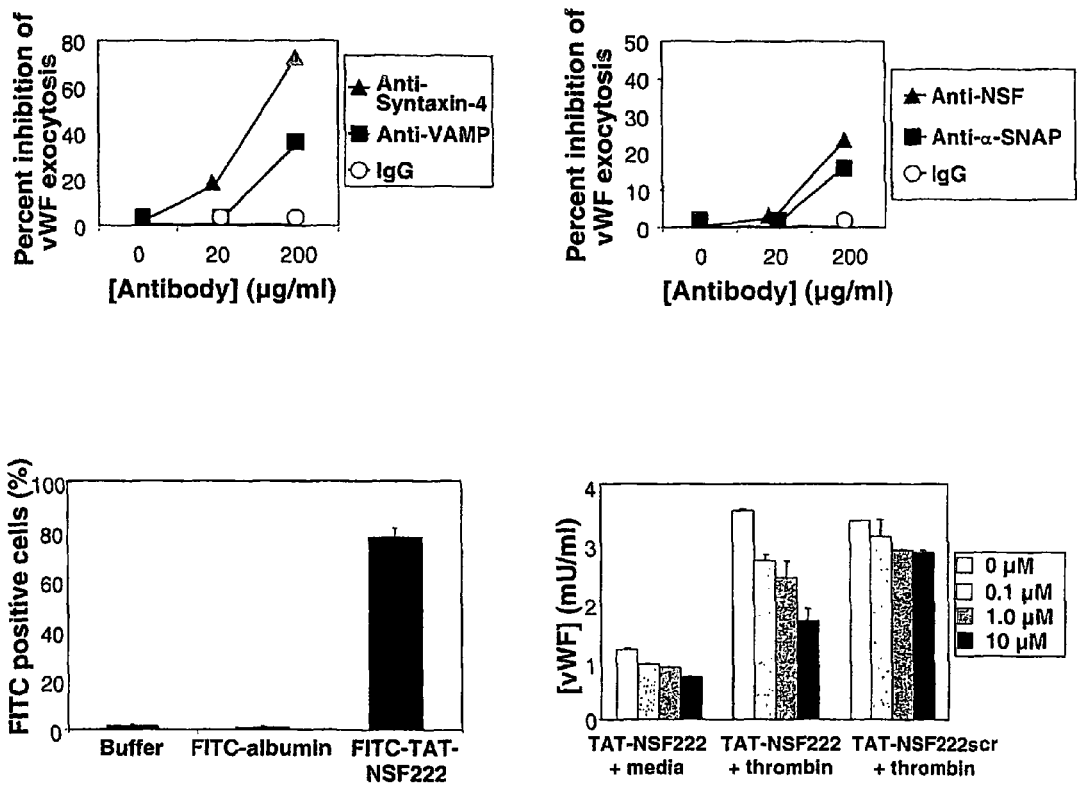
FIG. 2. NSF and SNARE molecules regulate Weibel-Palade body secretion. (A) Antibody to NSF inhibits Weibel-Palade body exocytosis. HAEC were permeabilized and incubated with antibody to NSF or α-SNAP. Cells were then resealed, treated with thrombin, and the amount of vWF released was measured as above (n=2). (B) NSF peptides enter HAEC. Cells were incubated with FITC labeled TAT-NSF peptide for 20 min, treated with ethidium bromide to quench extracellular FITC, and imaged by FACS (n=3±S.D.). (C) peptides inhibit vWF release. Cells were incubated with TAT-NSF peptides for 20 min, treated with media (left) or thrombin (middle and right), and the amount of released vWF was measured (n=3±S.D.).

The molecular machinery that regulates Weibel-Palade body exocytosis is unknown. However, since SNARE molecules regulate exocytosis of vesicles and granules from other cells, they might also regulate endothelial cell exocytosis of Weibel-Palade bodies as well. The expression of SNARE molecules in endothelial cells was first determined using brain extracts as a control. HAEC and human brain extracts were immunoblotted with antibodies to SNARE molecules. HAEC express VAMP-3, syntaxin-2 and syntaxin-4, and SNAP-23 (not shown). To explore the role of syntaxin-4 and VAMP-3 in the regulation of vWF release, HAEC were permeabilized, and then incubated with antibody to syntaxin-4, antibody to VAMP, or IgG as a control. Cells were then resealed, treated with thrombin, and the amount of vWF released into the media was measured. Antibody to syntaxin-4 inhibits vWF release by over 75% (FIG. 2A). Antibody that reacts with VAMP isoforms 1, 2, and 3 inhibits vWF release by approximately 25%.

These results suggest that SNARE molecules regulate Weibel-Palade body exocytosis.

NSF Regulates Weibel-Palade Body Exocytosis

The role of NSF in regulating Weibel-Palade body exocytosis was next explored. HAEC expression of NSF was first determined (not shown). Two approaches were then used to show that NSF regulates Weibel-Palade body exocytosis. The first approach involved antibody inhibition of exocytosis. HAEC were permeabilized as above, incubated with antibody to NSF or antibody to α-SNAP, resealed, and stimulated with thrombin. Antibody to NSF inhibits vWF release by approximately 25% (FIG. 2B). Antibody to α-SNAP also inhibits vWF release.

The second approach to demonstrating NSF regulation of Weibel-Palade body exocytosis involved peptide inhibition of NSF. A peptide inhibitor of NSF that crosses cell membranes was designed. This peptide, designated TAT-NSF222, includes the protein transduction domain of HIV TAT (residues 47-57) previously shown to transduce polypeptides into cells (Becker-Hapak et al., 2001), fused to a fragment of NSF (residues 222-243) previously shown to inhibit NSF (Schweizer et al., 1998). To show that this peptide enters HAEC, HAEC cells were incubated with 10 μM FITC-labeled TAT-NSF or 10 μM FITC-albumin for 20 min, ethidium bromide was added to quench extracellular fluorescence, and fluorescence of the cells was analyzed by FACS. Over 75% of cells treated with FITC-TAT-NSF222 contained FITC (FIG. 2C). HAEC were then incubated for 20 min with TAT-NSF222, or with a control peptide TAT-NSF222scr that consisted of the intact TAT domain followed by the amino acid residues of NSF 222-243 in a scrambled order. HAEC were transduced with TAT-NSF peptides, treated with media or thrombin, and the amount of vWF released into the media was measured by ELISA. TAT-NSF222 inhibits vWF release in a dose-dependent manner (FIG. 2D).

Taken together, the antibody and peptide inhibition data suggest that NSF regulates Weibel-Palade body exocytosis.

NO does not Inhibit NSF ATPase Activity

The effect of NO upon NSF activity was next explored, since NO inhibits Weibel-Palade body exocytosis, and since NSF regulates Weibel-Palade body exocytosis. The effect of NO upon the ATPase activity of NSF was first examined. DEA-NONOate was added to recombinant NSF, and the ATPase activity of NSF was measured. NO does not significantly inhibit NSF hydrolysis of ATP (FIG. 3A).

NO Inhibits NSF Disassembly Activity

The effect of NO upon NSF disassembly activity was next explored. ATP is required for NSF to disassemble the SNARE complex; ATP-γS can lock NSF onto the SNARE complex. The SNARE complex alone sediments at 7S, and the NSF-a-SNAP-SNARE complex sediments at approximately 20S. Accordingly, recombinant NSF was pre-treated with the NO donor DEA-NONOate 1 mM for 10 min. Pre-treated NSF, α-SNAP, and detergent extracts of HAEC membranes were then mixed in the presence of 0.5 mM ATP or ATP-γS. These reactions were then fractionated by sucrose density gradient ultracentrifugation, fractions were collected from the bottom of the tube, and immunoblotted with antibody to syntaxin-4. The SNARE complex sediments at 7S, as expected in the presence of NSF and ATP (not shown). The SNARE complex sediments at 20S, as expected in the presence of NSF and ATP-γS. However, the SNARE complex also sediments at 20S in the presence of ATP and NSF pre-treated with DEA-NONOate. These results suggest that NO inhibits the ability of NSF to disassemble a 20S SNARE complex derived from endothelial cell extracts.

The effect of NO upon NSF disassembly of purified, recombinant SNARE molecules was next examined. Recombinant (His)$_6$-NSF was pre-treated or not with 1 mM DEA-NONOate for 10 min, and then mixed with and (His)$_6$-α-SNAP and recombinant SNARE fusion polypeptides identified in endothelial cells: GST-syntaxin-4, VAMP-3, and SNAP-23. ATP or ATP-γS was added, the mixture was precipitated with glutathione-sepharose beads, and precipitated proteins were fractionated by SDS-PAGE and immunoblotted with antibody to the NSF tag.

NSF with α-SNAP interacts with GST-syntaxin-4 (not shown). ATP decreases the interaction of NSF with GST-syntaxin-4; ATP also decreases the co-precipitation of VAMP-3 and SNAP-23 along with GST-syntaxin-4, presumably by NSF disassembly of the SNARE complex. As expected, ATP-γS blocks NSF disassembly activity. However, NO blocks NSF disassembly of the SNARE complex, even in the presence of ATP (not shown). Furthermore, DTT restores the disassembly activity of NSF pre-treated with NO, suggesting that NO inhibition of NSF disassembly is reversible. Finally, NO inhibits NSF disassociation from GST-syntaxin-4 in a dose-dependent manner (not shown).

(The low level of interaction between NSF and SNAREs in the absence of adding additional ATP to the reaction mixture may be due to residual ATP in the storage buffer used to prepare recombinant NSF. Small amounts of ATP present in the reaction buffer may permit an interaction between NSF and SNAREs, while larger amounts enable NSF to disassemble the SNARE/α-SNAP/NSF complex.)

TAT-NSF Peptides Inhibit NSF ATPase Activity and NSF Disassociation from SNAREs

NO and TAT-NSF peptides inhibit NSF by different mechanisms. NO inhibits NSF disassembly activity but does not affect NSF ATPase activity, as shown above. In contrast, the TAT-NSF222 peptide inhibits both NSF ATPase activity (FIG. 3B) and also NSF disassembly activity (not shown). Thus the mechanisms by which NO and TAT-NSF peptides inhibit NSF are different: both inhibit NSF disassembly activity, but only TAT-NSF peptides inhibit NSF ATPase activity as well. Since NO reversibly inhibits NSF disassembly activity without affecting its ATPase activity, we reasoned that NO targets NSF cysteine residues in regions of NSF that couple the energy of ATP hydrolysis to the mechanical energy of disassembling the SNARE complex.

NO Inhibits Exocytosis by Inhibiting NSF

To confirm that NSF is a primary physiological target of NO, HAEC were pre-treated with 1 mM DEA-NONOate for 10 min to inhibit exocytosis, permeabilized as above, and then recombinant NSF 100 µg/ml was added. HAEC were then resealed, stimulated with thrombin, and the amount of vWF released into the media was measured. As before, NO inhibits exocytosis (FIG. 3C). However, exogenous recombinant NSF restores the ability of NO treated HAEC to undergo exocytosis (FIG. 3C). In contrast, recombinant NSF pre-treated with NO cannot restore the ability of NO treated HAEC to undergo exocytosis (FIG. 3C). These data suggest that NSF is indeed a primary target of NO in cells.

Cysteine Residues Mediate NSF Activity

NSF contains 9 cysteine residues, 3 in the N-terminal domain, 3 in the D1 domain, and 3 in the D2 domain (FIG. 4A). To determine the importance of individual cysteine residues in NSF functions, we made 9 individual NSF mutants, each lacking 1 of the 9 cysteine residues, and then compared the activity of wild-type NSF to mutant NSF.

A determination of which cysteine residues mediate NSF ATPase activity was made. The ATPase activity of wild-type NSF and of each NSF mutant was measured. Mutation of cysteine residues 21, 91, 264, and 334 partially decrease NSF ATPase activity (FIG. 4B, white bars).

Which cysteine residues mediate NSF interactions with SNARE molecules was next determined. The pull-down assay was repeated with wild-type and mutant NSF. NSF and α-SNAP were incubated with GST-SNARE fusion polypeptides in the presence of ATP or ATP-γS, and the mixture was precipitated with glutathione-sepharose beads, and finally immunoblotted with antibody to the NSF tag. Wild-type NSF interacts with GST-SNAREs in the presence of ATP-γS, and disassembles GST-SNAREs in the presence of ATP (not shown). Mutation of cysteine residues 250 and 599 have no effect on NSF interaction and disassembly activity. Mutation of cysteine residues 11, 21, 334, 568, and 582 block the ability of NSF to interact with GST-SNARE molecules. Mutation of cysteine residues 91 and 264 permit NSF to interact with the SNARE complex, but inhibit the ability of NSF to disassemble the GST-SNARE complex. These data suggest that one set of NSF cysteine residues regulate NSF interactions with SNARE complexes, and another set of NSF cysteine residues regulate NSF disassembly of SNARE complexes. In particular, cysteine residues 91 and 264 appear to regulate NSF disassembly activity.

NSF Cysteine Residue Targets of NO

NSF cysteine mutants were next used to explore which cysteine residues of NSF are targets of NO. NO was added to wild-type and mutant NSF, and the ATPase activity was measured. NO does not affect ATPase activity of wild-type NSF, and does not affect ATPase activity of any of the NSF mutants (FIG. 4B, black bars).

The effect of NO upon the disassembly activity of NSF mutants was then tested using the pull-down assay. NO blocks the ability of wild-type NSF to disassemble the SNARE complex in the presence of ATP (not shown). Mutation of cysteine residues 250 and 599 have no effect on the ability of NO to inhibit NSF disassembly activity. The effect of NO upon cysteine residues 11, 21, 334, 568, and 582 cannot be ascertained, since mutation of these residues abrogates NSF interaction with SNARE molecules. Mutation of cysteine residues 91 and 264 blocks the ability of NSF to disassemble the SNARE complex, and NO has no effect upon these mutants.

The number of cysteine residues that are nitrosylated by exogenous NO was next measured. Recombinant NSF was exposed to increasing amounts of DEA-NONOate, and then the Saville reaction was used to measure the number of nitrosocysteine residues per molecule of NSF. NO nitrosylates NSF in a dose-dependent manner (FIG. 4C). At 1 mM DEA-NONOate, approximately 3 cysteine residues are modified by NO per each molecule of NSF. (This dose of 1 mM DEA-NONOate also inhibits NSF disassembly activity as shown above.)

The cysteine residues that are targets of NO were identified by measuring the number of cysteines that are nitrosylated in wild-type and mutant NSF. DEA-NONOate was added to wild-type or mutant NSF that lack specific cysteine residues, and the Saville reaction was used to measure the number of nitrosocysteine residues per molecule of NSF. Mutation of cysteine residues 11, 250, 334, and 568 have no effect upon the nitrosocysteine content (FIG. 4D). However, mutation of cysteine residues 21, 91, or 264 decreases the nitrosocysteine content per NSF molecule by 1 (FIG. 4D). These data suggest that NO nitrosylates cysteine residues 21, 91, and 264 of NSF.

NO Nitrosylation of NSF is Reversible

Figure 5:
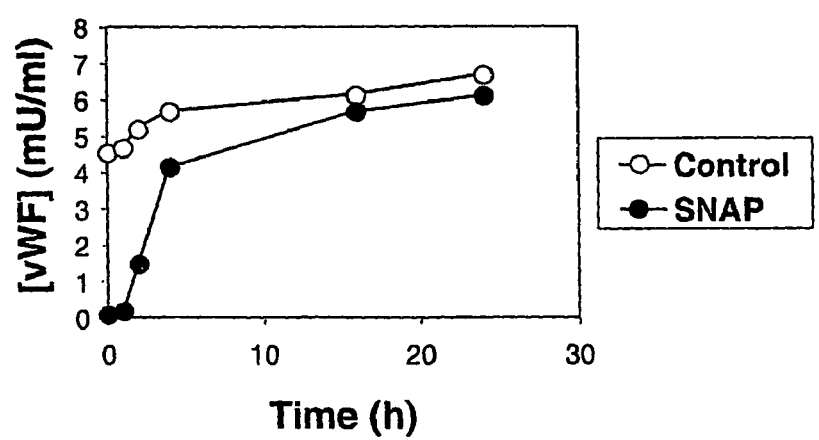
FIG. 5. NO inhibition of exocytosis and nitrosylation of NSF is reversible. (A) NO inhibition of exocytosis is temporary. HAEC were pre-treated with the NO donor SNAP 100 µM for 4 h, washed to remove the NO donor, and then at various times after NO treatment thrombin was added for 1 h, and the amount of vWF released into the media was measured (n=3±S.D.).
Figure 10:
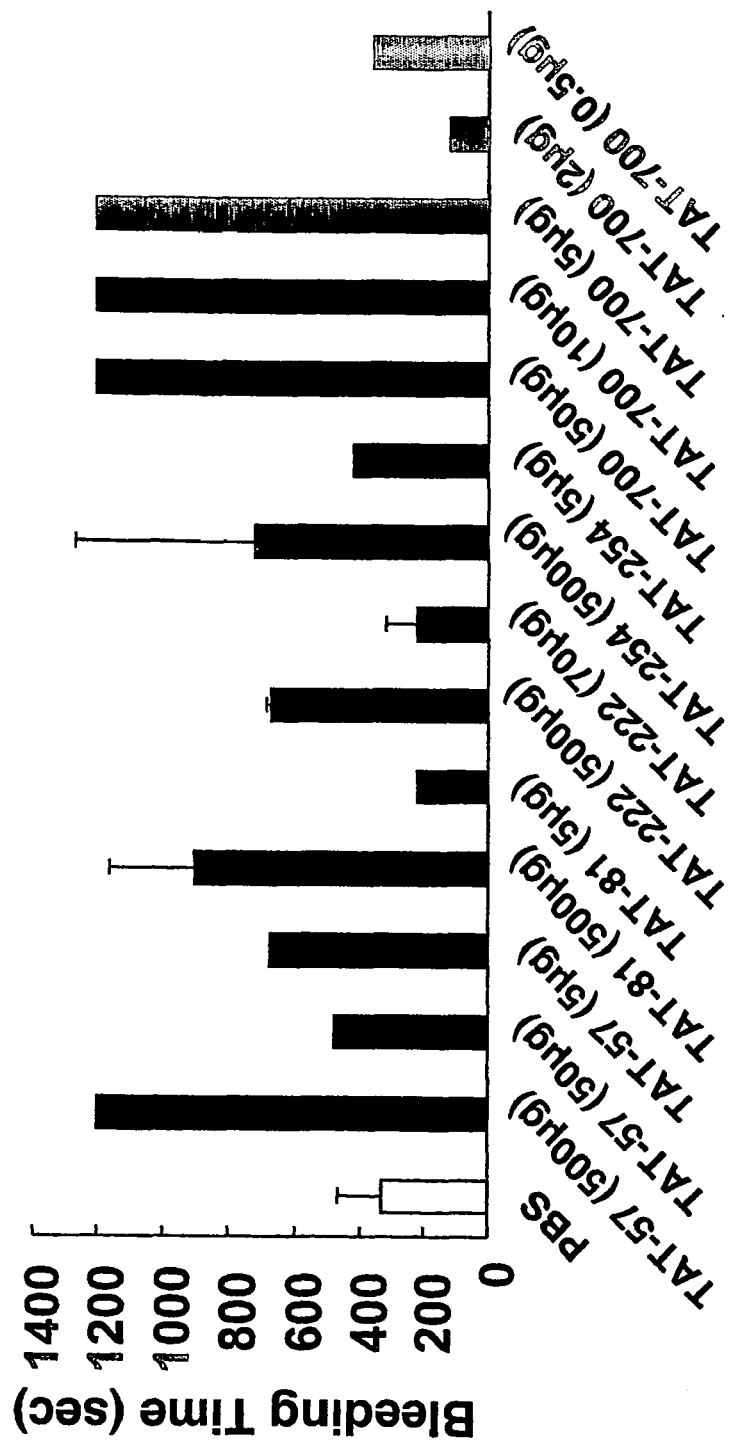
FIG. 10. Effect of TAT-NSF peptides on bleeding time in mice. Mice were injected with PBS or the TAT-NSF peptides that inhibits NSF, and after 45 min the distal tip of the tail was amputated and the bleeding time was measured (n=3±SD). If mice bled for more than 20 min, the experiment was stopped and the bleeding time was recorded as 20 min.

Since NSF plays a general role in vesicle trafficking, permanent inactivation of NSF would slow vesicular trafficking in general. However, local production of NO at the plasma membrane and reversible nitrosylation of NSF could provide spatial regulation of NSF. In order to measure how long NO inhibition of exocytosis lasts, HAEC were pre-treated with the NO donor SNAP 100 µM for 4 h, washed the cells to remove the NO donor, and then at various times afterwards stimulated the HAEC with thrombin, and the amount of vWF released into the media was measured. NO inhibits thrombin induced release of vWF, and a single application of NO continues to inhibit exocytosis 1 h after treatment (FIG. 5A). However, NO inhibition of exocytosis gradually decreases after 1-2 h; and 2-4 h after NO treatment about 75% of Weibel-Palade body exocytosis is restored (FIG. 5A). Thus NO inhibition of exocytosis is reversible.

In order to examine directly the reversibility of NSF nitrosylation, endothelial cells were pre-treated with an NO donor as above, and then cell lysates were harvested at various times after NO treatment. Cell lysates were immunoprecipitated with antibody to nitrosocysteine, fractionated by SDS-PAGE, and immunoblotted with antibody to NSF. Treatment with NO increases the level of nitrosylated NSF (not shown). The level of nitrosylated NSF decreases 2 h after treatment with NO, and 2-4 h after treatment the level of nitrosylated NSF is similar to non-treated cells (not shown). (In addition to the expected signal for NSF at 82 kD, another band at approximately 70 kD is observed.) Treatment with NO donors does not change the total amount of NSF for the first 4 h, but total amounts of NSF increase 4-16 h after NO treatment (not shown).

Taken together, these data show that within 2-4 h of exposure to NO, nitrosylation of NSF and inhibition of endothelial cell exocytosis is reversible.

NSF is Nitrosylated and Regulates Exocytosis In Vivo

In order to test whether or not NO modifies NSF in vivo, cell lysates were prepared from HAEC treated with media or the NOS inhibitor L-NAME. Polypeptides in this lysate containing nitrosothiols were biotinylated, precipitated with avidin-agarose, and immunoblotted with antibody to NSF (Jaffrey et al., 2001). NSF is nitrosylated in endothelial cells, and treatment of cells with increasing amounts of NOS inhibitor decreases NSF nitrosylation (not shown). A search for nitrosylated NSF in mice was undertaken. Polypeptides were prepared from spleens of wild-type and eNOS null mice as above. NSF is nitrosylated in wild-type mice expressing eNOS (not shown). In contrast, NSF is not nitrosylated in eNOS deficient mice. These data show that NO nitrosylates NSF in vivo.

To explore the physiological relevance of NSF regulation of Weibel-Palade body exocytosis, the effect of the NSF inhibitory peptide upon the bleeding time in mice was measured. Anesthetized mice were injected intravenously with saline, TAT-NSF222, or the control peptide TAT-NSF222scr; and after 45 min the distal 5 mm of tail was amputated and the bleeding time measured. (If the animals bled continuously for 20 min, the experiment was stopped, and the bleeding time was recorded as 20 min.) Treatment with saline or the control peptide has no effect upon bleeding time (FIG. 6A). In contrast, treatment with TAT-NSF222 dramatically prolongs the bleeding time (FIG. 6A). In fact, 3 of the 6 mice treated with the TAT-NSF222 peptide had bleeding times in excess of 20 min. (The NSF inhibitory peptides did not enter platelets and did not affect platelet exocytosis (data not shown). The NSF inhibitory peptides also did not affect vascular contractility of mouse aortas perfused in organ baths (data not shown).

These data show that NSF regulates Weibel-Palade body exocytosis in vivo, and suggest that NSF is a novel target for treatment of thrombotic and cardiovascular diseases.

NO Regulates Exocytosis In Vivo

The physiological relevance of NO regulation of Weibel-Palade body exocytosis was explored in two murine models. The bleeding time in wild-type and eNOS deficient mice was measured. Lack of eNOS decreases the bleeding time in mice, which would be predicted if a lack of NO decreased NSF inhibition and permitted an increase in exocytosis of vWF (FIG. 6B). We also measured serum levels of vWF and soluble P-selectin in wild-type and eNOS deficient mice. Serum levels of vWF are higher in eNOS deficient mice compared to wild-type mice (20±25 vs. 11±14 mU/ml, although these differences are not significant for n=6). Serum levels of soluble P-selectin are also higher in eNOS deficient mice compared to wild-type mice (81±21 vs. 73±14 mU/ml, although these differences are not significant for n=8). Conclusions from this physiological model of bleeding are limited because NO has effects upon platelets as well as endothelial cells. Despite the limitations of this in vivo model, increased levels of vWF and soluble P-selectin, and decreased bleeding times would be expected in eNOS deficient mice, if NO inhibits exocytosis in vivo.

To further examine the physiological relevance of NO regulation of Weibel-Palade body exocytosis, the effect of endogenous NO upon platelet interactions with endothelial cells in vivo was measured. Platelet rolling, or transient adherence of platelets to the walls of blood vessels, is mediated by vWF released by exocytosis (Andre et al., 2000). Inhibition of endogenous NO synthesis might permit an increase in Weibel-Palade body exocytosis, an increase in released vWF, and an increase in platelet adherence to venule walls. It was demonstrated that exogenous NO can inhibit histamine induced exocytosis from HAEC (FIG. 7A). Intravital microscopy was next employed to explore the effects of endogenous NO upon platelet rolling in vivo. Anesthetized mice were pre-treated or not with L-NAME, and then transfused with calcein-AM labeled platelets. The mesentery was externalized, superfused with histamine, and intravital microscopy was used to record interactions of fluorescently labeled platelets with mesenteric venules. Platelets were classified as adherent if they were transiently captured by the endothelium and then translocated in a stop-and-go fashion for a minimum of 2 seconds. Histamine rapidly induces platelet adhesion to the venule wall without aggregation, starting within 30 sec and peaking 3 min after histamine treatment (FIG. 7B). Inhibition of endogenous NOS with L-NAME increases histamine induced platelet interactions with the venule wall to a frequency more than double that observed in non-treated mice (FIG. 7B). Furthermore, inhibition of endogenous NOS permits an increase in platelet-venule interactions which finally peaks at 6 min after histamine treatment, indicating that the vWF release continues twice as long as in the control mice. This increase in transient platelet adherence to the venule would be predicted if less NO synthesis led to increased exocytosis of Weibel-Palade bodies and more release of vWF.

The bleeding time and platelet rolling data taken together suggest that NO regulates hemostatically important granule secretion in vivo.

Discussion

The major finding of this study is that NO regulates exocytosis by nitrosylating NSF, thereby inhibiting NSF disassembly activity. Inhibition of NOS increases endothelial release of vWF and increases platelet adherence to the stimulated vessel wall. Although NSF was originally purified as a protein necessary for intercisternal Golgi transport that was inhibited by NEM, this data suggests that NEM Sensitive Factor (NSF) is actually an NO Sensitive Factor.

Inhibition of NSF by NO

NO regulates a wide variety of proteins by nitrosylation of critical cysteine residues (Stamler, 1994; Stamler et al., 2001; Stamler et al., 1992). These data suggest that NO regulates NSF by covalently modifying cysteine residues of NSF C91 and C264. Since NO inhibits NSF disassembly activity but does not affect NSF ATPase activity, NO may uncouple the ability of NSF to convert the chemical energy of ATP hydrolysis into the mechanical energy necessary to separate the SNARE complex. NSF C91 is not adjacent to the N-terminal-D1 region linker, where its modification might influence a conformational change of NSF. However, NSF C264 is located within the D1 domain Walker A motif which interacts with ATP, and it is possible that nitrosylation of C264 may affect the efficiency by which ATP hydrolysis is converted into mechanical energy.

Importance of Cysteine Residues to NSF Function

These data emphasize the importance of cysteine residues to the function of NSF. Specific cysteine residues play a role in ATP hydrolysis: mutation of C21, C91, C264, and C334 reduces the ATPase activity of NSF by approximately 50% (FIG. 4B). C264 is located within the Walker A motif of the D1 domain, and C334 is located 3 residues away from the Walker B motif of the D1 domain, so mutation of these residues may alter ATP binding or hydrolysis. Specific cysteine residues C11, C21, C334, C568, and C582 are necessary for NSF to interact with the SNARE complex. Mutation of C11 and C21 in the N-terminal domain may interfere with the ability of NSF to interact with α-SNAP. Mutation of the cysteine residues C334 in the D1 domain and C568 and C582 in the D2 domain may affect the structure of NSF necessary for interaction with SNARE molecules. Finally, cysteine residues C91 and C264 are necessary for NSF to disassemble the SNARE complex.

NO Inhibition of NSF Inhibits Exocytosis

NO inhibition of NSF is a mechanism by which NO can regulate exocytosis. NSF is required for vesicle trafficking, although the precise stage at which it acts is unclear. NSF was originally thought to prime vesicles for fusion with target membranes. NSF activity is required prior to exocytosis in Drosophila (Littleton and Bellen, 1995; Littleton et al., 1998). The NSF homologue Sec18 is necessary prior to vacuole fusion in yeast (Mayer and Wickner, 1997; Mayer et al., 1996; Nichols et al., 1997). Finally, NSF and ATP are necessary for the incorporation of the rab effector EEA1 into the SNARE complex, which may mediate vesicle tethering prior to fusion (McBride et al., 1999). However, more recent data suggests that NSF regulates vesicle trafficking after fusion, disassembling the SNARE complex to permit recycling of individual SNARE molecules (Burgoyne and Morgan, 1998). It is also possible that NSF may play distinct roles in different organisms, or that NSF may regulate multiple stages of vesicle transport. Whether NSF regulates vesicle trafficking prior to or following membrane fusion, NSF is necessary for membrane fusion, and NO inhibition of NSF is a mechanism by which NO can regulate exocytosis.

Implications for Regulation of Exocytosis

NO inhibition of NSF is one possible mechanism for the anti-inflammatory effects of NO. NO derived from NOS3 in endothelial cells or NOS2 in macrophages can nitrosylate and inhibit NSF, decreasing Weibel-Palade body exocytosis, and limiting leukocyte rolling and activation. Conversely, lack of NO and increased Weibel-Palade body exocytosis may explain in part the increased risk for vascular inflammation and atherosclerosis in patients with impaired vascular NO synthesis. Finally, these observations may have significance for other areas of biology as well. NO nitrosylation of NSF may be a mechanism for regulation of a variety of physiological processes mediated by granule exocytosis, including neurotransmission, platelet thrombosis, and cytotoxic T lymphocyte killing.

Experimental Procedures

Materials

Thrombin was purchased from Enzyme Research Laboratories (South Bend, Ind.). Diethylamine (DEA)-NONOate and dithylenetriamine (DETA)-NONOate were purchased from Cayman Chemical (Ann Arbor, Mich.). Calcein-acetoxymethylester was purchased from Molecular Probes (Eugene, Ore.). Mouse monoclonal antibody to syntaxin-4 was from BD Biosciences (Bedford, Mass.). Rabbit polyclonal antibodies to NSF (H-300), a-SNAP (FL-295), and VAMP (FL-118) were from Santa Cruz Biotechnology, Inc. (Santa Cruz, Calif.). The antibody to nitrosocysteine was from Calbiochem (San Diego, Calif.). The cDNAs of RGS-$His_6$-NSF and RGS-$His_6$-a-SNAP were generous gifts from James E. Rothman (Rockefeller University, N.Y.). Mice were purchased from Jackson Laboratories (Bar Harbor, Me.).

Peptides

Peptides were synthesized by Anaspec Inc. (San Jose, Calif.). The TAT-NSF222 fusion polypeptide sequence is: YGRKKRRQRRR-GGG-LDKEFNSIFRRASRVFPPE (SEQ ID NO: 2). The control peptide TAT-NSF222scr sequence is: YGRKKRRQRRR-GGG-ENSFRFLADIFPA-KAFPVRFE (SEQ ID NO: 3).

Preparation of Recombinant NSF and SNARE Polypeptides

Recombinant RGS-$(His)_6$-NSF and RGS-$(His)6$-α-SNAP were expressed in bacteria and purified on a Ni-NTA-agarose column (HisTRAP, Amersham, Uppsala, Sweden). Recombinant GST-SNARE proteins were expressed in BL21 cells and purified with glutathione-agarose (GSTrap, Amersham). For some assays the GST tag was cleaved off of the GST-SNARE polypeptide with thrombin.

Cell Culture and Analysis of vWF Release

Human aortic endothelial cells (HAEC) and EGM-2 media were obtained from Clonetics (Walkersville, Md.). HAEC were pre-treated with NO donors, washed, stimulated with 1 U/mil of thrombin, and the amount of vWF released into the media was measured by an ELISA (American Diagnostica, Greenwich, Conn.). HAEC were permeabilized by incubation with 10 U/well of SLO (Sigma) in PBS pH 7.4 for 15 min at 37° C. (Walev et al., 2001). Some cells were incubated with 20-200 µg/ml of antibodies or with 100 µg/ml of recombinant NSF. Cells were then resealed by incubation with EGM-2 media for 4 h at 37° C., washed with EGM-2 media, and stimulated with thrombin as above.

ATPase Assay

The ATPase activity of NSF was measured by a coupled assay, in which ATP utilization is linked to the pyruvate kinase reaction, which generates pyruvate, which in turn is measured continuously with lactate dehydrogenase (Huang and Hackney, 1994). Recombinant NSF (0.2 µg/µl) was pre-treated with buffer or DEA or DEA-NONOate or NEM for 10 min at 22° C. ATPase reaction buffer (100 mM HEPES buffer, pH 7.0, 100 mM KCl, 10 mM $MgCl_2$, 5 mM $CaCl_2$, 10 mM ATP, 5 mM phosphoenol pyruvate, 50 U lactate dehydrogenase, and 50 U pyruvate kinase) was added to the mixture, followed by 10 µl of NADH (2 mg/ml in 1% sodium bicarbonate). The mixture was incubated for 10 min at 22° C., and the absorbance was measured at 340 nm.

NSF Disassembly Assay

Analysis of the 7S and 20S complexes was performed according to previously published protocols (Sollner et al., 1993). The disassembly activity of NSF was measured by a co-precipitation assay (Pevsner et al., 1994). Recombinant RGS-$(His)_6$-NSF (0.1 µg/µl) was pre-treated with buffer or 1.0 mM DEA or DEA-NONOate for 10 min at 22° C. Recombinant RGS-$(His)_6$-a-SNAP (0.1 µg/µl), and SNARE polypeptides (0.1 µg/µl each of VAMP-3, SNAP-23, and GST-Syntaxin-4) were added, followed by either 5 mM ATP/ 10 mM $MgCl_2$ or 5 mM ATP-gS/10 mM $MgCl_2$. This mixture of NSF and SNARE polypeptides was then incubated in binding buffer (4 mM HEPES pH 7.4, 0.1M NaCl, 1 mM EDTA, 3.5 mM $CaCl_2$, 3.5 mM $MgCl_2$, and 0.5% Nonidet P-40) and glutathione-sepharose beads for 1 h at 4° C. with rotation. The beads were washed with binding buffer 4 times, mixed with SDS-PAGE sample buffer, boiled for 3 min, and analyzed by immunoblotting.

Determination of S-Nitrosylation of NSF

Measurement of cysteine residues nitrosylated in vitro was performed by the Saville and Griess assays (Saura et al., 1999). Measurement of NSF nitrosylated in cultured cells was performed by immunoprecipitation with antibody to nitrosocysteine, followed by immunoblotting with antibody to NSF. Measurement of cysteine residues nitrosylated in vivo was performed as previously (Jaffrey et al., 2001; Jaffrey and Snyder, 2001).

Bleeding Times in Mice

Measurement of bleeding time in mice was performed as previously described (Weiss et al., 2002). Mice were anesthetized with an intramuscular injection of ketamine and xylazine, and 5 mm of the distal tip of the tail was amputated. The tail was blotted with filter paper every 5 sec until the paper was no longer stained. If the animals bled for 20 min, the experiment was stopped, and the bleeding time was recorded as 20 min.

Platelet Adherence to Venules in Mice

Measurements of platelet adherence in mice was adapted from Andre et al. (Andre et al., 2000). Mice were injected or not with 5 mg/kg L-NAME intravenously, and after 30 min transfused with calcein-acetoxymethylester (calcein-AM) labeled murine platelets (Denis et al., 1998). The animals were then prepared for intravital microscopy with an externalized mesentery (Ni et al., 2000). One mesenteric venule (130-180 µm in diameter) per animal was filmed for 2 min before and 20 min after a topical superfusion of 10 µl of 1 mM histamine. Platelet adherence was expressed as the number of adhering fluorescent cells per square millimeter of venular surface, calculated from the diameter and length of segment viewed.

References for Example 1

Andre, P., Denis, C. V., Ware, J., Saffaripour, S., Hynes, R. O., Ruggeri, Z. M., and Wagner, D. D. (2000). Platelets adhere to and translocate on von Willebrand factor presented by endothelium in stimulated veins. Blood 96, 3322-3328.

Becker-Hapak, M., McAllister, S. S., and Dowdy, S. F. (2001). TAT-mediated protein transduction into mammalian cells. Methods 24, 247-256.

Block, M. R., Glick, B. S., Wilcox, C. A., Wieland, F. T., and Rothman, J. E. (1988). Purification of an N-ethylmaleimide-sensitive protein catalyzing vesicular transport. Proc Natl Acad Sci USA 85, 7852-7856.

Bonfanti, R., Furie, B. C., Furie, B., and Wagner, D. D. (1989). PADGEM (GMP140) is a component of Weibel-Palade bodies of human endothelial cells. Blood 73, 1109-1112.

Burgoyne, R. D., and Morgan, A. (1998). Analysis of regulated exocytosis in adrenal chromaffin cells: insights into NSF/SNAP/SNARE function. Bioessays 20, 328-335.

Christopherson, K. S., and Bredt, D. S. (1997). Nitric oxide in excitable tissues: physiological roles and disease. J Clin Invest 100, 2424-2429.

Denis, C., Methia, N., Frenette, P. S., Rayburn, H., Ullman-Cullere, M., Hynes, R. O., and Wagner, D. D. (1998). A mouse model of severe von Willebrand disease: defects in hemostasis and thrombosis. Proc Natl Acad Sci USA 95, 9524-9529.

Huang, T. G., and Hackney, D. D. (1994). *Drosophila* kinesin minimal motor domain expressed in *Escherichia coli*. Purification and kinetic characterization. J Biol Chem 269, 16493-16501.

Huber, D., Cramer, E. M., Kaufmann, J. E., Meda, P., Masse, J. M., Kruithof, E. K., and Vischer, U. M. (2002). Tissue-type plasminogen activator (t-PA) is stored in Weibel-Palade bodies in human endothelial cells both in vitro and in vivo. Blood 99, 3637-3645.

Jaffrey, S. R., Erdjument-Bromage, H., Ferris, C. D., Tempst, P., and Snyder, S. H. (2001). Protein S-nitrosylation: a physiological signal for neuronal nitric oxide. Nat Cell Biol 3, 193-197.

Jaffrey, S. R., and Snyder, S. H. (2001). The biotin switch method for the detection of s-nitrosylated proteins. Sci STKE 2001, PL1.

Jahn, R., Lang, T., and Sudhof, T. C. (2003). Membrane fusion. Cell 112, 519-533.

Jahn, R., and Sudhof, T. C. (1999). Membrane fusion and exocytosis. Annu Rev Biochem 68, 863-911.

Kaiser, C. A., and Schekman, R. (1990). Distinct sets of SEC genes govern transport vesicle formation and fusion early in the secretory pathway. Cell 61, 723-733.

Kuhlencordt, P. J., Chen, J., Han, F., Astern, J., and Huang, P. L. (2001a). Genetic deficiency of inducible nitric oxide synthase reduces atherosclerosis and lowers plasma lipid peroxides in apolipoprotein E-knockout mice. Circulation 103, 3099-3104.

Kuhlencordt, P. J., Gyurko, R., Han, F., Scherrer-Crosbie, M., Aretz, T. H., Hajjar, R., Picard, M. H., and Huang, P. L. (2001b). Accelerated atherosclerosis, aortic aneurysm formation, and ischemic heart disease in apolipoprotein E/endothelial nitric oxide synthase double-knockout mice. Circulation 104, 448-454.

Littleton, J. T., and Bellen, H. J. (1995). Presynaptic proteins involved in exocytosis in *Drosophila melanogaster*: a genetic analysis. Invert Neurosci 1, 3-13.

Littleton, J. T., Chapman, E. R., Kreber, R., Garment, M. B., Carlson, S. D., and Ganetzky, B. (1998). Temperature-sensitive paralytic mutations demonstrate that synaptic exocytosis requires SNARE complex assembly and disassembly. Neuron 21, 401-413.

Malhotra, V., Orci, L., Glick, B. S., Block, M. R., and Rothman, J. E. (1988). Role of an N-ethylmaleimide-sensitive transport component in promoting fusion of transport vesicles with cisternae of the Golgi stack. Cell 54, 221-227.

May, A. P., Whiteheart, S. W., and Weis, W. I. (2001). Unraveling the mechanism of the vesicle transport ATPase NSF, the N-ethylmaleimide-sensitive factor. J Biol Chem 276, 21991-21994.

Mayadas, T. N., Johnson, R. C., Rayburn, H., Hynes, R. O., and Wagner, D. D. (1993). Leukocyte rolling and extravasation are severely compromised in P selectin-deficient mice. Cell 74, 541-554.

Mayer, A., and Wickner, W. (1997). Docking of yeast vacuoles is catalyzed by the Ras-like GTPase Ypt7p after symmetric priming by Sec18p (NSF). J Cell Biol 136, 307-317.

Mayer, A., Wickner, W., and Haas, A. (1996). Sec18p (NSF)-driven release of Sec17p (alpha-SNAP) can precede docking and fusion of yeast vacuoles. Cell 85, 83-94.

McBride, H. M., Rybin, V., Murphy, C., Giner, A., Teasdale, R., and Zerial, M. (1999). Oligomeric complexes link Rab5 effectors with NSF and drive membrane fusion via interactions between EEA1 and syntaxin 13. Cell 98, 377-386.

McEver, R. P., Beckstead, J. H., Moore, K. L., Marshall-Carlson, L., and Bainton, D. F. (1989). GMP-140, a platelet alpha-granule membrane protein, is also synthesized by vascular endothelial cells and is localized in Weibel-Palade bodies. J Clin Invest 84, 92-99.

Mellman, I., and Warren, G. (2000). The road taken: past and future foundations of membrane traffic. Cell 100, 99-112.

Michel, T., and Feron, O. (1997). Nitric oxide synthases: which, where, how, and why? J Clin Invest 100, 2146-2152.

Nathan, C., and Xie, Q. W. (1994). Nitric oxide synthases: roles, tolls, and controls. Cell 78, 915-918.

Ni, H., Denis, C. V., Subbarao, S., Degen, J. L., Sato, T. N., Hynes, R. O., and Wagner, D. D. (2000). Persistence of platelet thrombus formation in arterioles of mice lacking both von Willebrand factor and fibrinogen. J Clin Invest 106, 385-392.

Nichols, B. J., Ungermann, C., Pelham, H. R., Wickner, W. T., and Haas, A. (1997). Homotypic vacuolar fusion mediated by t- and v-SNAREs. Nature 387, 199-202.

Papapetropoulos, A., Rudic, R. D., and Sessa, W. C. (1999). Molecular control of nitric oxide synthases in the cardiovascular system. Cardiovasc Res 43, 509-520.

evsner, J., Hsu, S. C., and Scheller, R. H. (1994). n-Sec1: a neural-specific syntaxin-binding protein. Proc Natl Acad Sci USA 91, 1445-1449.

Qian, Z., Gelzer-Bell, R., Yang Sx, S. X., Cao, W., Ohnishi, T., Wasowska, B. A., Hruban, R. H., Rodriguez, E. R., Baldwin, W. M., 3rd, and Lowenstein, C. J. (2001). Inducible nitric oxide synthase inhibition of Weibel-Palade body release in cardiac transplant rejection. Circulation 104, 2369-2375.

Radomski, M. W., and Moncada, S. (1993). Regulation of vascular homeostasis by nitric oxide. Thromb Haemost 70, 36-41.

Rothman, J. E., and Wieland, F. T. (1996). Protein sorting by transport vesicles. Science 272, 227-234.

Rudic, R. D., Shesely, E. G., Maeda, N., Smithies, O., Segal, S. S., and Sessa, W. C. (1998). Direct evidence for the importance of endothelium-derived nitric oxide in vascular remodeling. J Clin Invest 101, 731-736.

Ruggeri, Z. M. (1997). von Willebrand factor. J Clin Invest 100, S41-46.

Saura, M., Zaragoza, C., McMillan, A., Quick, R. A., Hohenadl, C., Lowenstein, J. M., and Lowenstein, C. J. (1999). An antiviral mechanism of nitric oxide: inhibition of a viral protease. Immunity 10, 21-28.

Schweizer, F. E., Dresbach, T., DeBello, W. M., O'Connor, V., Augustine, G. J., and Betz, H. (1998). Regulation of neurotransmitter release kinetics by NSF. Science 279, 1203-1206.

Sollner, T., Whiteheart, S. W., Brunner, M., Erdjument-Bromage, H., Geromanos, S., Tempst, P., and Rothman, J. E. (1993). SNAP receptors implicated in vesicle targeting and fusion. Nature 362, 318-324.

Springer, S., Spang, A., and Schekman, R. (1999). A primer on vesicle budding. Cell 97, 145-148.

Stamler, J. S. (1994). Redox signaling: nitrosylation and related target interactions of nitric oxide. Cell 78, 931-936.

Stamler, J. S., Lamas, S., and Fang, F. C. (2001). Nitrosylation the prototypic redox-based signaling mechanism. Cell 106, 675-683.

Stamler, J. S., Singel, D. J., and Loscalzo, J. (1992). Biochemistry of nitric oxide and its redox-activated forms. Science 258, 1898-1902.

Vischer, U. M., and Wagner, D. D. (1993). CD63 is a component of Weibel-Palade bodies of human endothelial cells. Blood 82, 1184-1191.

Wagner, D. D. (1993). The Weibel-Palade body: the storage granule for von Willebrand factor and P-selectin. Thromb Haemost 70, 105-110.

Wagner, D. D., Olmsted, J. B., and Marder, V. J. (1982). Immunolocalization of von Willebrand protein in Weibel-Palade bodies of human endothelial cells. J Cell Biol 95, 355-360.

Walev, I., Bhakdi, S. C., Hofmann, F., Djonder, N., Valeva, A., Aktories, K., and Bhakdi, S. (2001). Delivery of proteins into living cells by reversible membrane permeabilization with streptolysin-O. Proc Natl Acad Sci USA 98, 3185-3190.

Weibel, E. R., and Palade, J. E. (1964). New cytoplasmic components in arterial endothelium. Journal of Cell Biology 23, 101-106.

Weiss, E. J., Hamilton, J. R., Lease, K. E., and Coughlin, S. R. (2002). Protection against thrombosis in mice lacking PAR3. Blood 100, 3240-3244.

Wickner, W., and Haas, A. (2000). Yeast homotypic vacuole fusion: a window on organelle trafficking mechanisms. Annu Rev Biochem 69, 247-275.

Example 2

A Novel Class of Fusion Polypeptides Inhibits Exocytosis

The preceding example showed that NSF regulates exocytosis of endothelial granules and that nitric oxide (NO) regulates exocytosis by chemically modifying NSF. Based on these observations, additional novel peptide inhibitors that block exocytosis by inhibiting NSF were developed.

Design of Peptide Inhibitors of NSF

A set of fusion polypeptide inhibitors of NSF was designed. The amino terminus of the fusion peptide is an 11 amino acid residue polypeptide fragment derived from the human immunodeficiency virus TAT domain (YGRKKRRQRRR, SEQ ID NO: 1). This domain can efficiently deliver peptides and polypeptides into cells. (Becker-Hapak et al., 2001; Schwarze et al., 1999; Vocero-Akbani et al., 2001; Vocero-Akbani et al., 2000) The central domain of the fusion polypeptide contains a linker composed of the amino acid residues GGG. The carboxy terminus of the fusion peptide is derived from various domains of NSF. Domains of NSF of 20-25 amino acid residues from regions that have been shown to be critical for NSF function were selected.

A set of 5 fusion polypeptide inhibitors of NSF, which we refer to as TAT-NSF fusion polypeptides, were designed. In this series, all TAT-NSF peptides contain the identical TAT domain (YGRKKRRQRRR, SEQ ID NO: 1) and the same linker (GGG). However, each TAT-NSF peptide contains a unique NSF domain. NSF domains were selected that mediate important functions of NSF, such as binding to Soluble NSF attachment protein (SNAP), interacting with nitric oxide, or regulating SNARE disassembly (Table 1). Each TAT-NSF peptide is identified by a number corresponding to the amino terminal amino acid residue of the NSF peptide. For example, TAT-NSF222 is composed of 11 amino acids of the HIV TAT polypeptide followed by a 6 amino acid linker followed by 23 amino acids of the NSF D1 domain, residues 222-243 (GLDKEFNSIFRRAFASRVFPPE, SEQ ID NO: 4). The sequence of the entire fusion peptide designated TAT-NSF222 is YGRKKRRQRRR-GGG-GLDKEFNSIFRRAFASRVFPPE (SEQ ID NO: 2).

TABLE 1

Design of TAT-NSF polypeptides.

| ID | NSF Residues | TAT-linker-NSF Sequence | SEQ ID NO: |
|---|---|---|---|
| TAT-NSF57 | 57-77 | YGRKKRRQRRR-GGG-GSVAFSLPQRKWAGLSIGQE | 5 |
| TAT-NSF81 | 81-101 | YGRKKRRQRRR-GGG-ALYSFDKAKQCIGTMTIEID | 6 |
| TAT-NSF222 | 222-243 | YGRKKRRQRRR-GGG-GLDKEFNSIFRRAFASRVFPPE | 2 |
| TAT-NSF254 | 254-274 | YGRKKRRQRRR-GGG-KGILLYGPPGCGKTLLARQIG | 7 |
| TAT-NSF700 | 700-720 | YGRKKRRQRRR-GGG-LLDYVPIGPRFSNLVLQALLVL | 8 |

TAT-NSF Peptides Inhibit NSF ATPase Activity

The effect of the TAT-NSF peptide inhibitors upon the ability of NSF to hydrolyze ATP was measured. 10 μM TAT-NSF peptides was added to recombinant NSF, and the hydrolysis of ATP was measured. All 5 TAT-NSF peptides inhibited NSF ATPase activity (FIG. 8A). TAT-NSF81 (SEQ ID NO: 6) and TAT-NSF700 (SEQ ID NO: 8) were more effective than the other peptides. The effects of TAT-NSF81 (SEQ ID NO: 6) upon NSF were further defined. TAT-NSF81 (SEQ ID NO: 6) inhibits NSF ATPase activity in a dose-dependent manner with an IC50% between 1-10 µM (FIG. 8B).

These data show that TAT-NSF peptides inhibit NSF ATPase activity.

TAT-NSF Peptides Inhibit NSF Disassembly Activity

The effect of the TAT-NSF peptide inhibitors upon the ability of NSF to separate from SNARE complexes was measured. Recombinant NSF was pre-treated with 1 µM TAT-NSF peptides, and recombinant GST-SNARE polypeptides were then added, including syntaxin-4, SNAP-23, and VAMP-3. ATP was added to enable NSF to separate from the SNARE molecules. The GST-SNARE molecules were precipitated with glutathione-agarose, and the precipitants immunoblotted for NSF. As a control, ATP-γS was added to lock NSF onto the SNARE complex.

The effect of TAT-NSF peptides on NSF disassembly activity was determined. (His)$_6$-NSF was pre-treated or not with 1 µM TAT-peptides, and incubated with a-SNAP and GST-SNARE fusion polypeptides expressed in endothelial cells. ATP or ATP-γS was added, and the mixture was precipitated with glutathione-sepharose. Precipitated proteins were immunoblotted with antibody to the NSF tag. As expected, NSF bound to SNAREs in the presence of ATP-γS, and NSF released SNAREs in the presence of ATP (not shown). However, TAT-NSF peptides blocked NSF release of SNAREs, even in the presence of ATP.

TAT-NSF81 (SEQ ID NO: 6) inhibition of NSF disassembly activity was also investigated. Increasing amounts of recombinant NSF were pre-treated with TAT-NSF81 (SEQ ID NO: 6) for 20 min, mixed with a-SNAP and endothelial cell GST-SNARE fusion polypeptides as above. ATP was added, GST-SNAREs were precipitated with glutathione-sepharose, and the precipitant was analyzed for the co-precipitation of NSF. TAT-NSF81 (SEQ ID NO: 6) was shown to inhibit NSF separation from SNAREs in a dose dependent manner with an IC50% of between 0.1-1.0 µM (not shown).

These data show that TAT-NSF peptides block NSF separation from SNAREs.

TAT-NSF Peptides Inhibit Endothelial Cell Exocytosis.

The ability of TAT-NSF to affect exocytosis from cells was investigated. Endothelial cells release vWF by exocytosis when stimulated by thrombin. Accordingly, endothelial cells were incubated with increasing amounts of TAT-NSF peptides for 20 min, then treated with 1 U/ml thrombin, and the amount of vWF released into the media was measured by ELISA.

TAT-NSF peptides inhibit endothelial exocytosis of vWF (FIG. 2A). TAT-NSF81 (SEQ ID NO: 6) and TAT-NSF700 (SEQ ID NO: 8) are most effective at inhibiting release of vWF. We further defined the potency of TAT-NSF81 (SEQ ID NO: 6) by adding increasing concentrations of TAT-NSF81 (SEQ ID NO: 6) to endothelial cells, and then triggering exocytosis with thrombin, and measuring vWF release. TAT-NSF81 (SEQ ID NO: 6) inhibits endothelial exocytosis with an IC50% between 1-10 µM (FIG. 2B).

TAT-NSF Peptides Prolong Bleeding of Mice

The effect of TAT-NSF peptides in vivo was explored. The time for hemostasis to occur after injury to a blood vessel depends in part upon endothelial exocytosis of vWF. Because TAT-NSF peptides could enter endothelial cells, block exocytosis of vWF, and decrease platelet adherence to the endothelium, and bleeding time should be prolonged. Mice were injected intravenously with increasing amounts of TAT-NSF peptides, anesthetized after 45 min, and the 0.5 cm distal tip of the tail amputated. The time to hemostasis was measured. (Bleeding times longer than 20 min were recorded as 20 min, and the mouse was then sacrificed.)

TAT-NSF peptides increase the bleeding time in a dose-dependent manner (FIG. 3). TAT-NSF57 (SEQ ID NO: 5) and TAT-NSF700 (SEQ ID NO: 8) were the most efficacious peptides, prolonging the bleeding time over 20 min. TAT-NSF700 (SEQ ID NO: 8) was the most potent peptide, with an IC50% between 2-5 µg/mouse. These data demonstrate that TAT-NSF peptides can regulate critical vascular functions such as maintenance of hemostasis.

Discussion

A novel class of peptides that inhibits exocytosis in vitro and in vivo has been invented. These peptides are designed to enter cells and inhibit NSF, a key regulator of exocytosis. Mice injected with these peptides have prolonged bleeding times, demonstrating that these peptides have striking in vivo effects.

Peptide Transduction of Cells and Animals

Fusion polypeptides that contain a TAT domain, which enables the peptide to cross cell membranes and enter cells, were designed. Three polypeptides have been identified which can translocate across cell membranes: the HIV TAT polypeptide, the Antennapedia polypeptide of *Drosophila*, and the VP22 polypeptide from herpes simplex virus (HSV) (Becker-Hapak et al., 2001; Schwarze et al., 1999; Vocero-Akbani et al., 2001; Vocero-Akbani et al., 2000). The mechanism by which these polypeptides enter cells is unclear. Recently, Dowdy and colleagues showed that TAT peptides may enter cells through a process by micropinocytosis (Wadia et al., 2004). In the present investigations, the TAT domain was chosen as the amino terminal region of the fusion polypeptides, since the TAT domain should translocate the NSF inhibitory domain across the plasma membrane and into cells.

The data show a direct vascular effect of TAT-NSF peptides: TAT-NSF peptides prolong the bleeding time. These data suggest that TAT-fusion polypeptides are a novel method of transducing vascular cells.

Polypeptide Inhibition of NSF Blocks Exocytosis

Fusion polypeptides that contain a domain of NSF were designed in order to inhibit NSF and decrease exocytosis. The data demonstrate that the TAT-NSF polypeptides inhibit NSF ATPase activity and inhibit NSF disassembly activity. Although NSF is required for vesicle trafficking, the precise stage at which it acts is unclear. NSF may prime vesicles for fusion with target membranes prior to exocytosis, or NSF may act after exocytosis by disassembling SNARE complexes to permit cycling of individual SNARE components (Mayer and Wickner, 1997; Mayer et al., 1996; Nichols et al., 1997; Burgoyne and Morgan, 1998). Whether NSF regulates vesicle trafficking before or after membrane fusion, NSF is necessary for exocytosis. Taken together, our data suggest that our TAT-NSF polypeptide inhibitors directly inhibit NSF. Exocytosis as a Novel Drug Target Exocytosis as a Novel Drug Target Endothelial exocytosis plays a critical role in vascular homeostasis, regulating platelet and leukocyte adherence to endothelial cells. Quiescent endothelial cells do not release granules, but a variety of stimuli can activate endothelial exocytosis, promoting thrombosis and vascular inflammation. Exocytosis is thus an attractive target for therapy. Compound that target exocytosis such as TAT-NSF polypeptides may represent a new class of therapeutic agents that are effective in the treatment of thrombotic and inflammatory disorders.

Experimental Procedures

Materials

Thrombin was purchased from Enzyme Research Laboratories (South Bend, Ind.). Mouse monoclonal antibody to syntaxin-4 was from BD Biosciences (Bedford, Mass.). Rabbit polyclonal antibodies to NSF (H-300) were from Santa Cruz Biotechnology, Inc. (Santa Cruz, Calif.). The cDNAs of RGS-His$_6$-NSF and RGS-His$_6$-α-SNAP were a gift. Mice were purchased from Jackson Laboratories (Bar Harbor, Me.).

Peptides

Peptides were synthesized by Anaspec Inc. (San Jose, Calif.) and by the Johns Hopkins University School of Medicine Peptide Synthesis Facility.

Preparation of Recombinant NSF and SNARE Polypeptides

Recombinant RGS-(His)$_6$-NSF and RGS-(His)$_6$-α-SNAP were expressed in bacteria and purified on a Ni-NTA-agarose column (HisTRAP, Amersham, Uppsala, Sweden). Recombinant GST-SNARE proteins were expressed in BL21 cells and purified with glutathione-agarose (GSTrap, Amersham). For some assays the GST tag was cleaved off of the GST-SNARE polypeptide with thrombin.

Cell Culture and Analysis of vWF Release

Human aortic endothelial cells (HAEC) and EGM-2 media were obtained from Clonetics (Walkersville, Md.). HAEC were pre-treated with TAT-NSF peptides for 20 min, washed, stimulated with 1 U/ml of thrombin, and the amount of vWF released into the media was measured by an ELISA (American Diagnostica, Greenwich, Conn.).

ATPase Assay

The ATPase activity of NSF was measured by a coupled assay, in which ATP utilization is linked to the pyruvate kinase reaction, which generates pyruvate, which in turn is measured continuously with lactate dehydrogenase (Huang and Hackney, 1994). Recombinant NSF (0.2 μg/μl) was pre-treated with buffer or TAT-NSF peptides for 10 min at 22° C. ATPase reaction buffer (100 mM HEPES buffer, pH 7.0, 100 mM KCl, 10 mM MgCl$_2$, 5 mM CaCl$_2$, 10 mM ATP, 5 mM phosphoenol pyruvate, 50 U lactate dehydrogenase, and 50 U pyruvate kinase) was added to the mixture, followed by 10 μl of NADH (2 mg/ml in 1% sodium bicarbonate). The mixture was incubated for 10 min at 22° C., and the absorbance was measured at 340 nm.

NSF Disassembly Assay

The disassembly activity of NSF was measured by a co-precipitation assay (Pevsner et al., 1994). Recombinant RGS-(His)$_6$-NSF (0.1 μg/μl) was pre-treated with buffer or TAT-NSF peptides for 10 min at 22 ûC. Recombinant RGS-(His)$_6$-α-SNAP (0.1 μg/μl), and SNARE polypeptides (0.1 μg/μl each of VAMP-3, SNAP-23, and GST-Syntaxin-4) were added, followed by either 5 mM ATP/10 mM MgCl$_2$ or 5 mM ATP-γS/10 mM MgCl$_2$. This mixture of NSF and SNARE polypeptides was then incubated in binding buffer (4 mM HEPES pH 7.4, 0.1M NaCl, 1 mM EDTA, 3.5 mM CaCl$_2$, 3.5mM MgCl$_2$, and 0.5% Nonidet P-40) and glutathione-sepharose beads for 1 h at 4° C. with rotation. The beads were washed with binding buffer 4 times, mixed with SDS-PAGE sample buffer, boiled for 3 min, and analyzed by immunoblotting for NSF.

Bleeding Times in Mice

Measurement of bleeding time in mice was performed as previously described (Weiss et al., 2002). Mice were anesthetized with an intramuscular injection of ketamine and xylazine, and 5 mm of the distal tip of the tail was amputated. The tail was immersed in warmed PBS and the time until cessation of bleeding was recorded. If the animals bled for 20 min, the experiment was stopped, and the bleeding time was recorded as 20 min.

References for Example 2

Babor, S. M., and Fass, D. (1999). Crystal structure of the Sec18p N-terminal domain. Proc Natl Acad Sci USA 96, 14759-14764.

Becker-Hapak, M., McAllister, S. S., and Dowdy, S. F. (2001). TAT-mediated protein transduction into mammalian cells. Methods 24, 247-256.

Birch, K. A., Ewenstein, B. M., Golan, D. E., and Pober, J. S. (1994). Prolonged peak elevations in cytoplasmic free calcium ions, derived from intracellular stores, correlate with the extent of thrombin-stimulated exocytosis in single human umbilical vein endothelial cells. J Cell Physiol 160, 545-554.

Block, M. R., Glick, B. S., Wilcox, C. A., Wieland, F. T., and Rothman, J. E. (1988). Purification of an N-ethylmaleimide-sensitive protein catalyzing vesicular transport. Proc Natl Acad Sci USA 85, 7852-7856.

Burgoyne, R. D., and Morgan, A. (1998). Analysis of regulated exocytosis in adrenal chromaffin cells: insights into NSF/SNAP/SNARE function. Bioessays 20, 328-335.

Datta, Y. H., Romano, M., Jacobson, B. C., Golan, D. E., Serhan, C. N., and Ewenstein, B. M. (1995). Peptido-leukotrienes are potent agonists of von Willebrand factor secretion and P-selectin surface expression in human umbilical vein endothelial cells. Circulation 92, 3304-3311.

Ferro-Novick, S., and Jahn, R. (1994). Vesicle fusion from yeast to man. Nature 370, 191-193.

Foreman, K. E., Vaporciyan, A. A., Bonish, B. K., Jones, M. L., Johnson, K. J., Glovsky, M. M., Eddy, S. M., and Ward, P. A. (1994). C5a-induced expression of P-selectin in endothelial cells. J Clin Invest 94, 1147-1155.

Hanson, P. I., Roth, R., Morisaki, H., Jahn, R., and Heuser, J. E. (1997). Structure and conformational changes in NSF and its membrane receptor complexes visualized by quick-freeze/deep-etch electron microscopy. Cell 90, 523-535.

Huang, T. G., and Hackney, D. D. (1994). *Drosophila* kinesin minimal motor domain expressed in *Escherichia coli*. Purification and kinetic characterization. J Biol Chem 269, 16493-16501.

Lenzen, C. U., Steinmann, D., Whiteheart, S. W., and Weis, W. I. (1998). Crystal structure of the hexamerization domain of N-ethylmaleimide-sensitive fusion protein. Cell 94, 525-536.

Malhotra, V., Orci, L., Glick, B. S., Block, M. R., and Rothman, J. E. (1988). Role of an N-ethylmaleimide-sensitive transport component in promoting fusion of transport vesicles with cisternae of the Golgi stack. Cell 54, 221-227.

Matsushita, K., Morrell, C. N., Cambien, B., Yang, S. X., Yamakuchi, M., Bao, C., Hara, M. R., Quick, R. A., Cao, W., O'Rourke, B., et al. (2003). Nitric oxide regulates exocytosis by S-nitrosylation of N-ethylmaleimide-sensitive factor. Cell 115, 139-150.

Matveeva, E. A., He, P., and Whiteheart, S. W. (1997). N-Ethylmaleimide-sensitive fusion protein contains high and low affinity ATP-binding sites that are functionally distinct. J Biol Chem 272, 26413-26418.

May, A. P., Misura, K. M., Whiteheart, S. W., and Weis, W. I. (1999). Crystal structure of the amino-terminal domain of N-ethylmaleimide-sensitive fusion protein. Nat Cell Biol 1, 175-182.

Mayer, A., and Wickner, W. (1997). Docking of yeast vacuoles is catalyzed by the Ras-like GTPase Ypt7p after symmetric priming by Sec18p (NSF). J Cell Biol 136, 307-317.

Mayer, A., Wickner, W., and Haas, A. (1996). Sec18p (NSF)-driven release of Sec17p (alpha-SNAP) can precede docking and fusion of yeast vacuoles. Cell 85, 83-94.

Nagiec, E. E., Bernstein, A., and Whiteheart, S. W. (1995). Each domain of the N-ethylmaleimide-sensitive fusion protein contributes to its transport activity. J Biol Chem 270, 29182-29188.

Neuwald, A. F., Aravind, L., Spouge, J. L., and Koonin, E. V. (1999). AAA+: A class of chaperone-like ATPases associated with the assembly, operation, and disassembly of protein complexes. Genome Res 9, 27-43.

Nichols, B. J., Ungermann, C., Pelham, H. R., Wickner, W. T., and Haas, A. (1997). Homotypic vacuolar fusion mediated by t- and v-SNAREs. Nature 387, 199-202.

Patel, S., and Latterich, M. (1998). The AAA team: related ATPases with diverse functions. Trends Cell Biol 8, 65-71.

Pevsner, J., Hsu, S. C., and Scheller, R. H. (1994). n-Sec1: a neural-specific syntaxin-binding protein. Proc Natl Acad Sci USA 91, 1445-1449.

Rothman, J. E. (1994). Mechanisms of intracellular protein transport. Nature 372, 55-63.

Rowe, T., and Balch, W. E. (1997). Membrane fusion. Bridging the gap by AAA ATPases. Nature 388, 20-21.

Schwarze, S. R., Ho, A., Vocero-Akbani, A., and Dowdy, S. F. (1999). In vivo protein transduction: delivery of a biologically active protein into the mouse. Science 285, 1569-1572.

Sollner, T., Bennett, M. K., Whiteheart, S. W., Scheller, R. H., and Rothman, J. E. (1993). A protein assembly-disassembly pathway in vitro that may correspond to sequential steps of synaptic vesicle docking, activation, and fusion. Cell 75, 409-418.

Steel, G. J., and Morgan, A. (1998). Selective stimulation of the D1 ATPase domain of N-ethylmaleimide-sensitive fusion protein (NSF) by soluble NSF attachment proteins. FEBS Lett 423, 113-116.

Tagaya, M., Wilson, D. W., Brunner, M., Arango, N., and Rothman, J. E. (1993). Domain structure of an N-ethylmaleimide-sensitive fusion protein involved in vesicular transport. J Biol Chem 268, 2662-2666.

Utgaard, J. O., Jahnsen, F. L., Bakka, A., Brandtzaeg, P., and Haraldsen, G. (1998). Rapid secretion of prestored interleukin 8 from Weibel-Palade bodies of microvascular endothelial cells. J Exp Med 188, 1751-1756.

Vischer, U. M., Jornot, L., Wollheim, C. B., and Theler, J. M. (1995). Reactive oxygen intermediates induce regulated secretion of von Willebrand factor from cultured human vascular endothelial cells. Blood 85, 3164-3172.

Vischer, U. M., and Wollheim, C. B. (1997). Epinephrine induces von Willebrand factor release from cultured endothelial cells: involvement of cyclic AMP-dependent signaling in exocytosis. Thromb Haemost 77, 1182-1188.

Vocero-Akbani, A., Chellaiah, M. A., Hruska, K. A., and Dowdy, S. F. (2001). Protein transduction: delivery of Tat-GTPase fusion proteins into mammalian cells. Methods Enzymol 332, 36-49.

Vocero-Akbani, A., Lissy, N. A., and Dowdy, S. F. (2000). Transduction of full-length Tat fusion proteins directly into mammalian cells: analysis of T cell receptor activation-induced cell death. Methods Enzymol 322, 508-521.

Wadia, J. S., Stan, R. V., and Dowdy, S. F. (2004). Transducible TAT-HA fusogenic peptide enhances escape of TAT-fusion proteins after lipid raft macropinocytosis. Nat Med 10, 310-315.

Wagner, D. D. (1993). The Weibel-Palade body: the storage granule for von Willebrand factor and P-selectin. Thromb Haemost 70, 105-110.

Weber, T., Zemelman, B. V., McNew, J. A., Westermann, B., Gmachl, M., Parlati, F., Sollner, T. H., and Rothman, J. E. (1998). SNAREpins: minimal machinery for membrane fusion. Cell 92, 759-772.

Weiss, E. J., Hamilton, J. R., Lease, K. E., and Coughlin, S. R. (2002). Protection against thrombosis in mice lacking PAR3. Blood 100, 3240-3244.

Whiteheart, S. W., Rossnagel, K., Buhrow, S. A., Brunner, M., Jaenicke, R., and Rothman, J. E. (1994). N-ethylmaleimide-sensitive fusion protein: a trimeric ATPase whose hydrolysis of ATP is required for membrane fusion. J Cell Biol 126, 945-954.

Whiteheart, S. W., Schraw, T., and Matveeva, E. A. (2001). N-ethylmaleimide sensitive factor (NSF) structure and function. Int Rev Cytol 207, 71-112.

Wolff, B., Burns, A. R., Middleton, J., and Rot, A. (1998). Endothelial cell "memory" of inflammatory stimulation: human venular endothelial cells store interleukin 8 in Weibel-Palade bodies. J Exp Med 188, 1757-1762.

Yu, R. C., Hanson, P. I., Jahn, R., and Brunger, A. T. (1998). Structure of the ATP-dependent oligomerization domain of N-ethylmaleimide sensitive factor complexed with ATP. Nat Struct Biol 5, 803-811.

Example 3

TAT-NSF Peptides Decrease Size of Myocardial Infarction

The ability of the fusion peptides of the present invention to impact cardiac infraction was investigated. Mice were pretreated intravenously with vehicle or 5 ug/mouse TAT-NSF700 (SEQ ID NO: 8) peptide 15 min prior to infarction. Myocardial infarctions were created in mice by ligation of the left anterior descending coronary artery. Myocardial ischemia was maintained for 35 minutes, and then the ligation of the coronary artery was released, and reperfusion continued for 24 h.

The mice were then sacrificed and the size of the myocardial infarction was quantitated as previously done (Jones S P, Greer J J, Kakkar A K, Ware P D, Turnage R H, Hicks M, van Haperen R, de Crom R, Kawashima S, Yokoyama M, Lefer D J. Am J Physiol Heart Circ Physiol. 2004 January; 286(1): H276-82. Epub 2003 Sep. 11.). The area at risk (AAR) was measured with Evans blue dye, the left ventricle (LV) area was measured by planimetery, and the infarct area (INF) was measured with TTC staining. There were 7 mice per group.

Figure 11:
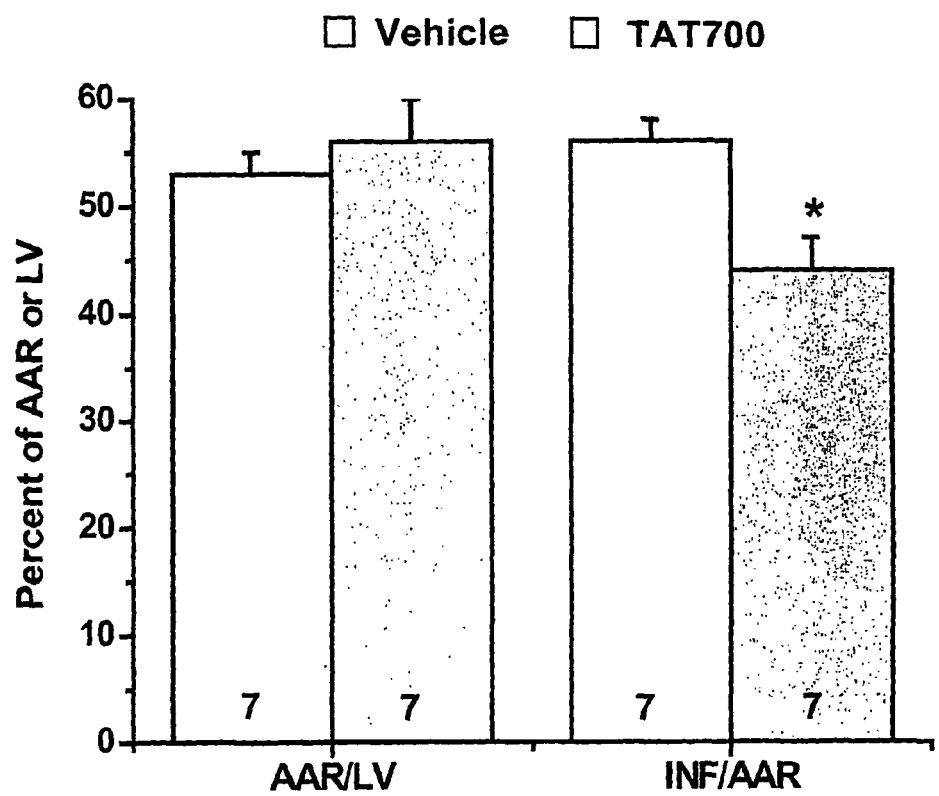
FIG. 11. Effect of TAT-NSF peptides on infraction size in mice. White columns represent mice treated with vehicle; gray columns represent mice treated with TAT-700.

The results of the study are given in FIG. 11. As can be seen, the size of the infarct in vehicle treated mice was 56%+/−2. In contrast, the size of the infarct in TAT-NSF peptide treated mice was 44%+/−3. Thus the TAT-NSF peptide treatment caused an absolute reduction in infarct size of 12%, and a relative reduction of 21%.

These data show that TAT-NSF peptides decrease the size of myocardial infarctions.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A fusion peptide comprising,
   a first sequence which promotes translocation of said fusion peptide across a membrane, and
   a second sequence that inhibits N-ethylmaleimide sensitive factor (NSF) activity, wherein said fusion peptide is SEQ ID NO: 8.

2. The fusion peptide of claim 1, wherein said membrane is an endothelial cell membrane.

* * * * *

SEQUENCE LISTING

<160> NUMBER OF SEQ ID NOS: 12

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 36
<212> TYPE: PRT
<213> ORGANISM: Artificial
<220> FEATURE:
<223> OTHER INFORMATION: fusion peptide

<400> SEQUENCE: 2

Tyr Gly Arg Lys Lys Arg Arg Gln Arg Arg Gly Gly Gly Gly Leu
1               5                   10                  15

Asp Lys Glu Phe Asn Ser Ile Phe Arg Arg Ala Phe Ala Ser Arg Val
            20                  25                  30

Phe Pro Pro Glu
        35

<210> SEQ ID NO 3
<211> LENGTH: 35
<212> TYPE: PRT
<213> ORGANISM: Artificial
<220> FEATURE:
<223> OTHER INFORMATION: fusion peptide

<400> SEQUENCE: 3

Tyr Gly Arg Lys Lys Arg Arg Gln Arg Arg Gly Gly Gly Glu Asn
1               5                   10                  15

Ser Phe Arg Phe Leu Ala Asp Ile Phe Pro Ala Lys Ala Phe Pro Val
            20                  25                  30

Arg Phe Glu
        35

<210> SEQ ID NO 4
<211> LENGTH: 22
<212> TYPE: PRT
<213> ORGANISM: Homo sapiens

<400> SEQUENCE: 4

Gly Leu Asp Lys Glu Phe Asn Ser Ile Phe Arg Arg Ala Phe Ala Ser
1               5                   10                  15

Arg Val Phe Pro Pro Glu
            20

<210> SEQ ID NO 5
<211> LENGTH: 34
<212> TYPE: PRT
<213> ORGANISM: Artificial
<220> FEATURE:
<223> OTHER INFORMATION: fusion peptide

<400> SEQUENCE: 5

Tyr Gly Arg Lys Lys Arg Arg Gln Arg Arg Gly Gly Gly Gly Ser
1               5                   10                  15

```
Val Ala Phe Ser Leu Pro Gln Arg Lys Trp Ala Gly Leu Ser Ile Gly
            20                  25                  30

Gln Glu

<210> SEQ ID NO 6
<211> LENGTH: 34
<212> TYPE: PRT
<213> ORGANISM: Artificial
<220> FEATURE:
<223> OTHER INFORMATION: fusion peptide

<400> SEQUENCE: 6

Tyr Gly Arg Lys Lys Arg Arg Gln Arg Arg Gly Gly Gly Ala Leu
1               5                   10                  15

Tyr Ser Phe Asp Lys Ala Lys Gln Cys Ile Gly Thr Met Thr Ile Glu
            20                  25                  30

Ile Asp

<210> SEQ ID NO 7
<211> LENGTH: 35
<212> TYPE: PRT
<213> ORGANISM: Artificial
<220> FEATURE:
<223> OTHER INFORMATION: fusion peptide

<400> SEQUENCE: 7

Tyr Gly Arg Lys Lys Arg Arg Gln Arg Arg Gly Gly Gly Lys Gly
1               5                   10                  15

Ile Leu Leu Tyr Gly Pro Pro Gly Cys Gly Lys Thr Leu Leu Ala Arg
            20                  25                  30

Gln Ile Gly
        35

<210> SEQ ID NO 8
<211> LENGTH: 36
<212> TYPE: PRT
<213> ORGANISM: Artificial
<220> FEATURE:
<223> OTHER INFORMATION: fusion peptide

<400> SEQUENCE: 8

Tyr Gly Arg Lys Lys Arg Arg Gln Arg Arg Gly Gly Gly Leu Leu
1               5                   10                  15

Asp Tyr Val Pro Ile Gly Pro Arg Phe Ser Asn Leu Val Leu Gln Ala
            20                  25                  30

Leu Leu Val Leu
        35

<210> SEQ ID NO 9
<211> LENGTH: 20
<212> TYPE: PRT
<213> ORGANISM: Homo sapiens

<400> SEQUENCE: 9

Gln Ser Val Ile Ser Pro Asp Trp Asp Phe Thr Lys Met Gly Ile Gly
1               5                   10                  15

Gly Leu Asp Lys
        20

<210> SEQ ID NO 10
<211> LENGTH: 22
<212> TYPE: PRT
<213> ORGANISM: Homo sapiens
```

```
<400> SEQUENCE: 10

Gly Leu Asp Lys Glu Phe Asn Ser Ile Phe Arg Arg Ala Phe Ala Ser
1               5                   10                  15

Arg Val Phe Pro Pro Glu
            20

<210> SEQ ID NO 11
<211> LENGTH: 20
<212> TYPE: PRT
<213> ORGANISM: Homo sapiens

<400> SEQUENCE: 11

Thr Gly Lys Thr Leu Ile Ala Arg Lys Ile Gly Thr Met Leu Asn Ala
1               5                   10                  15

Arg Glu Pro Lys
            20

<210> SEQ ID NO 12
<211> LENGTH: 19
<212> TYPE: PRT
<213> ORGANISM: Homo sapiens

<400> SEQUENCE: 12

Lys Tyr Val Gly Glu Ser Glu Ala Asn Val Arg Arg Leu Phe Ala Glu
1               5                   10                  15

Ala Glu Glu
```